United States Patent
Okazoe et al.

(10) Patent No.: US 9,260,383 B2
(45) Date of Patent: Feb. 16, 2016

(54) METHOD FOR PRODUCING CARBAMATE COMPOUND, CARBAMATE COMPOUND, AND METHOD FOR PRODUCING ISOCYANATE COMPOUND USING SAME

(71) Applicant: Asahi Glass Company, Limited, Tokyo (JP)

(72) Inventors: Takashi Okazoe, Tokyo (JP); Yuko Nagasaki, Tokyo (JP); Hidekazu Okamoto, Tokyo (JP)

(73) Assignee: ASAHI GLASS COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/555,092

(22) Filed: Nov. 26, 2014

(65) Prior Publication Data

US 2015/0087854 A1    Mar. 26, 2015

Related U.S. Application Data

(60) Division of application No. 13/630,915, filed on Sep. 28, 2012, now Pat. No. 8,927,756, which is a continuation of application No. PCT/JP2011/056095, filed on Mar. 15, 2011.

(30) Foreign Application Priority Data

Apr. 2, 2010   (JP) ................................. 2010-086126

(51) Int. Cl.
| | |
|---|---|
| C07C 271/24 | (2006.01) |
| C07C 271/20 | (2006.01) |
| C07C 263/04 | (2006.01) |
| C07C 269/04 | (2006.01) |

(52) U.S. Cl.
CPC .............. C07C 271/24 (2013.01); C07C 263/04 (2013.01); C07C 269/04 (2013.01); C07C 271/20 (2013.01); *C07C 2101/14* (2013.01)

(58) Field of Classification Search
CPC .... C07C 271/20; C07C 271/24; C07C 269/04
See application file for complete search history.

(56) References Cited

U.S. PATENT DOCUMENTS

| 2003/0125579 A1 | 7/2003 | Yoshida et al. |
| 2009/0082588 A1 | 3/2009 | Polo et al. |
| 2012/0231376 A1 | 9/2012 | Rölle et al. |

FOREIGN PATENT DOCUMENTS

| CN | 1727330 A | 2/2006 |
| CN | 101602694 A | 12/2009 |
| JP | 59-088453 | 5/1984 |
| JP | 01-230550 A | 9/1989 |
| JP | 06-298717 A | 10/1994 |
| JP | 08-259482 A | 10/1996 |
| JP | 2002-500654 A | 1/2002 |
| JP | 2003-252846 A | 9/2003 |
| JP | 4298995 | 4/2009 |
| JP | 2009-108034 A | 5/2009 |
| JP | 4328109 | 6/2009 |
| WO | WO-98/54128 A1 | 12/1998 |
| WO | WO-99/47493 A1 | 9/1999 |
| WO | WO 0035998 A2 * | 6/2000 ............ C07C 233/63 |
| WO | WO-2009/098327 A1 | 8/2009 |
| WO | WO 2011/054795 A1 | 5/2011 |

OTHER PUBLICATIONS

International Search Report issued in PCT/JP2011/056095 dated Jun. 14, 2011.
Toshio Nishikawa et al., "One-Pot Transformation of Trichloroacetamide into Readily Deprotectable Carbamates", Organic Letters, 2006, vol. 8, No. 15, 3263-3265.
European Search Report corresponding to Application No. 11765331.1, dated Jul. 2, 2015. 6 pages

* cited by examiner

Primary Examiner — Yong Chu
(74) Attorney, Agent, or Firm — Foley & Lardner LLP

(57) ABSTRACT

The present invention relates to a method of producing a carbamate compound, comprising reacting a fluorine-containing carbonic diester compound represented by formula (1) and a non-aromatic diamine compound represented by formula (2) without using a catalyst, to thereby produce a carbamate compound represented by formula (3), and a method of producing an isocyanate compound represented by formula (20) from the carbamate compound without using a catalyst, wherein R represents a fluorine-containing monovalent aliphatic hydrocarbon group, and A represents a divalent aliphatic hydrocarbon group, a divalent alicyclic hydrocarbon group or a divalent aromatic-aliphatic hydrocarbon group.

[Chem. 1]

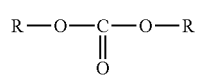

(1)

[Chem. 2]

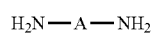

(2)

[Chem. 3]

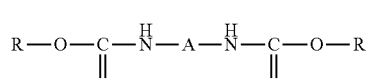

(3)

[Chem. 4]

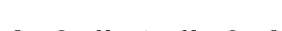

(20)

1 Claim, 1 Drawing Sheet

# METHOD FOR PRODUCING CARBAMATE COMPOUND, CARBAMATE COMPOUND, AND METHOD FOR PRODUCING ISOCYANATE COMPOUND USING SAME

CROSS REFERENCE TO RELATED APPLICATIONS

This application is a Divisional of U.S. application Ser. No. 13/630,915, filed Sep. 28, 2012, issued as U.S. Pat. No. 8,927,756, which is a Continuation application filed under 35 U.S.C. 111(a) claiming the benefit under 35 U.S.C. §§120 and 365(c) of PCT International Application No. PCT/JP2011/056095 filed on Mar. 15, 2011, which is based upon and claims the benefit of priority of Japanese Application No. 2010-086126 filed on Apr. 2, 2010, the entire contents of which are hereby incorporated by reference in their entireties.

TECHNICAL FIELD

This invention relates to a method of producing a carbamate compound, a carbamate compound obtained by the method and a method of producing an isocyanate compound using the carbamate compound.

BACKGROUND OF THE INVENTION

Isocyanate compounds are industrially broadly used as materials of, for example, various urethane compounds and urea compounds; and curing agents of resins and paints.

For example, the following methods are known as the method of producing isocyanate compounds.

(1) A method of reacting a primary amine with phosgene. This is mainly used industrially.

(2) A method of thermally decomposing a carbamate compound having —N(H)—C(O)O— in its molecule in the presence of a catalyst (e.g. Patent Reference 1).

(3) A method in which a non-aromatic carbamate compound is obtained by reacting a non-aromatic diamine, which does not have such a structure that the amino groups directly bonded to an aromatic ring, with an alkylaryl carbonate in the absence of a catalyst, and then it is converted into an isocyanate compound by thermal decomposition in the presence of a catalyst (Patent Reference 2).

(4) A method of obtaining an isocyanate compound by thermally decomposing an aromatic carbamate compound having a fluorine atom in its molecule in the absence of a catalyst (Patent Reference 3).

(5) A method in which a carbamate compound having a fluorine atom in its molecule is obtained by reacting a polyamine and a fluorine-containing carbonic diester in the presence of a catalyst, and then it is converted into an isocyanate compound by thermal decomposition in the absence of a catalyst (Patent References 4 and 5).

(6) A method of obtaining an isocyanate compound by a de-chloroform reaction of trichloroacetamides in N,N-dimethylformamide in the presence of sodium carbonate (Non-patent Reference 1).

CITATION LIST

Patent Literature

Patent Reference 1: Japanese Patent No. 4328109
Patent Reference 2: Japanese Patent No. 4298995
Patent Reference 3: JP-T-2002-500654
Patent Reference 4: JP-A-2009-108034
Patent Reference 5: WO 2009/098327

Non Patent Literature

Non-patent Reference 1: ORGANIC LETTERS, 2006, vol. 8, no. 15, p. 3263-3265

SUMMARY OF THE INVENTION

Technical Problem

However, the method of the above-mentioned (1) is difficult to handle because phosgene has toxicity.

The method of the above-mentioned (2) requires a catalyst for accelerating the thermal decomposition because the thermal decomposition rate of the carbamate compound is very slow. When such a catalyst is used, it becomes necessary to carry out an operation of separating the catalyst after obtaining the target isocyanate compound. However, this poses problems such that, for example, the separation operation is not easy, and the amount of the target compound formed per unit mass of the catalyst is small.

The method of the above-mentioned (3) can provide a non-aromatic carbamate compound without using a catalyst, but the conversion of the obtained non-aromatic carbamate compound into an isocyanate compound still requires a catalyst, so that the problems due to the use of a catalyst cannot be solved.

The method of the above-mentioned (4) is limited to a method of obtaining an aromatic isocyanate compound without a catalyst from an aromatic carbamate compound.

The method of the above-mentioned (5) requires a catalyst at the time of obtaining a fluorine-containing carbamate compound from a fluorine-containing carbonic diester compound, so that the problems due to the use of a catalyst cannot be solved.

The method of the above-mentioned (6) also requires a catalyst, so that the problems due to the use of a catalyst cannot be solved.

The invention has been made in order to solve the above-mentioned problems, and it provides: a method of producing a carbamate compound that can provide an isocyanate compound with using neither phosgene nor a catalyst; a carbamate compound obtained by the method; and a method of producing an isocyanate compound using the carbamate compound.

Means for Solving the Problem

As described above, the above-mentioned patent references 3 to 5 each disclose a method of obtaining an isocyanate compound without using a catalyst from a carbamate compound having a fluorine atom in its molecule. However, as is described in the patent references 4 and 5, it has been considered that a catalyst is necessary for producing such a carbamate compound having a fluorine atom in its molecule.

Specifically, paragraph [0081] of the patent reference 4 discloses an example in which an aromatic fluorine-containing dicarbamate compound was produced by reacting 2,4-toluenediamine and bis(trifluoroethyl)carbonate at 140° C.

for 20 hours using phosphagen as a catalyst, and paragraph [0082] thereof discloses a comparative example showing that the aromatic fluorine-containing dicarbamate compound was not formed even by the same reaction carried out at 140° C. for 20 hours if phosphagen serving as the catalyst was not added.

In addition, Example 2.5. on page 30 of the publication of patent reference 5 discloses an example in which an aliphatic fluorine-containing dicarbamate compound was produced by reacting 1,2-ethylenediamine with bis(trifluoroethyl)carbonate in the presence of a specified catalyst.

However, the present inventors have found a method by which a carbamate compound can be obtained, without using a catalyst, from a fluorine-containing carbonic diester compound and a non-aromatic diamine compound and also an isocyanate compound can be produced from the thus obtained carbamate compound without using a catalyst, thereby resulting in the accomplishment of the invention.

That is, the present invention provides a method of producing a carbamate compound, comprising reacting a fluorine-containing carbonic diester compound represented by formula (1) and a non-aromatic diamine compound represented by formula (2) without using a catalyst, to thereby produce a carbamate compound represented by formula (3).

[Chem. 1]

$$R-O-\underset{\underset{O}{\|}}{C}-O-R \qquad (1)$$

(wherein, R represents a fluorine-containing monovalent aliphatic hydrocarbon group)

[Chem. 2]

$$H_2N\text{-}A\text{-}NH_2 \qquad (2)$$

(wherein, A represents a divalent aliphatic hydrocarbon group, a divalent alicyclic hydrocarbon group or a divalent aromatic-aliphatic hydrocarbon group)

[Chem. 3]

$$R-O-\underset{\underset{O}{\|}}{C}-\underset{H}{N}-A-\underset{H}{N}-\underset{\underset{O}{\|}}{C}-O-R \qquad (3)$$

(wherein, R represents a fluorine-containing monovalent aliphatic hydrocarbon group, and A represents a divalent aliphatic hydrocarbon group, a divalent alicyclic hydrocarbon group or a divalent aromatic-aliphatic hydrocarbon group)

R of formula (1) preferably has no fluorine atom on the α-position carbon atom bonded to the oxygen atom of the carbonate bond, and preferably has two or more groups, in total, of at least one member selected from the group consisting of a fluorine atom, a polyfluoroalkyl group and a perfluoroalkyl group bonded to the adjacent β-position carbon atom.

R of formula (1) is preferably any of:
2,2,3,3-tetrafluoro-n-propyl group,
2,2,3,3,3-pentafluoro-n-propyl group,
1,1,1,3,3,3-hexafluoro-1-propyl group,
2,2,3,3,3,4,4,5,5-octafluoro-n-pentyl group,
2,2,3,4,4,4-hexafluoro-n-butyl group, or
2,2,2-trifluoroethyl group.

The non-aromatic diamine compound represented by formula (2) is preferably any of:
1,6-hexamethylenediamine,
isophoronediamine,
1,3-bis(aminomethyl)cyclohexane,
1,4-bis(aminomethyl)cyclohexane,
4,4'-diamino(dicyclohexylmethane),
2,5-bis(aminomethyl)bicyclo[2,2,1]heptane,
2,6-bis(aminomethyl)bicyclo[2,2,1]heptane,
1,3-bis(aminomethyl)benzene, or
1,4-bis(aminomethyl)benzene.

The present invention provides a carbamate compound obtained by the production method of the present invention.

The carbamate compound is preferably the carbamate compound represented by any of formulae (4) to (19).

[Chem. 4]

(4)

XDC-1

[Chem. 5]

(5)

XDC-2

-continued
[Chem. 6]
(6)
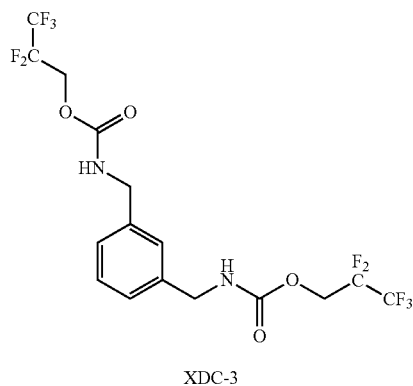
XDC-3
[Chem. 7]
(7)
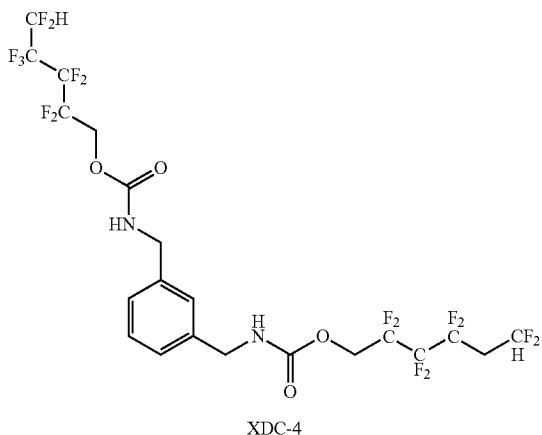
XDC-4
[Chem. 8]
(8)
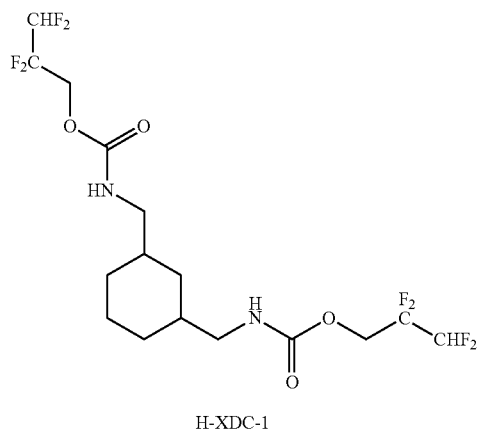
H-XDC-1
[Chem. 9]
(9)
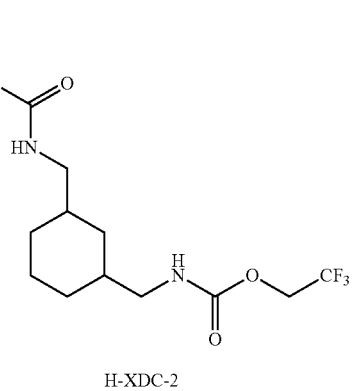
H-XDC-2
[Chem. 10]
(10)
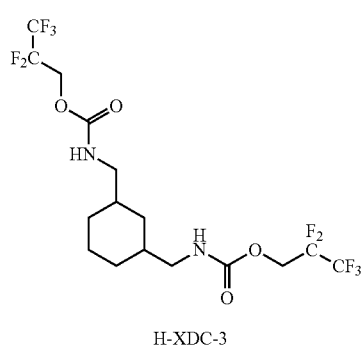
H-XDC-3
[Chem. 11]
(11)
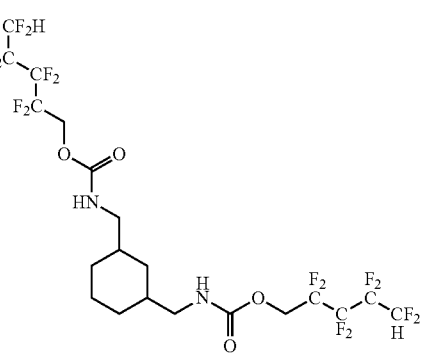
H-XDC-4
[Chem. 12]
(12)
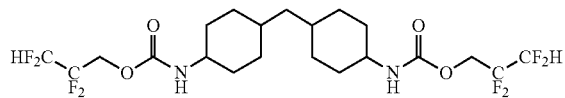
H-MDC-1
[Chem. 13]
(13)
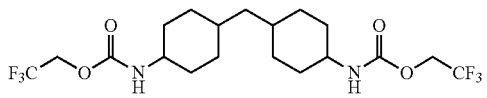
H-MDC-2

-continued

[Chem. 14]

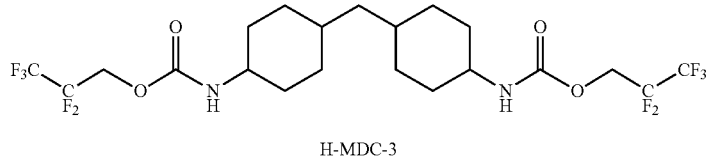

H-MDC-3

(14)

[Chem. 15]

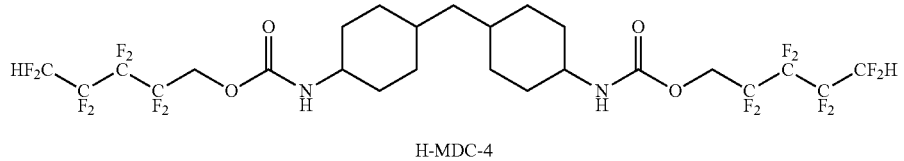

H-MDC-4

(15)

[Chem. 16]

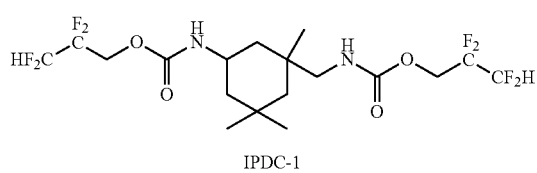

IPDC-1

(16)

[Chem. 17]

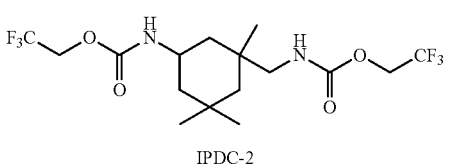

IPDC-2

(17)

[Chem. 18]

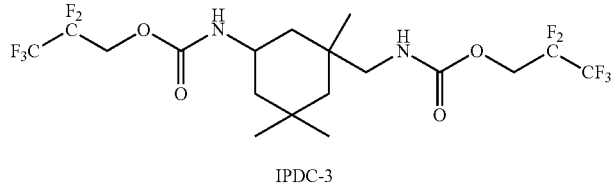

IPDC-3

(18)

[Chem. 19]

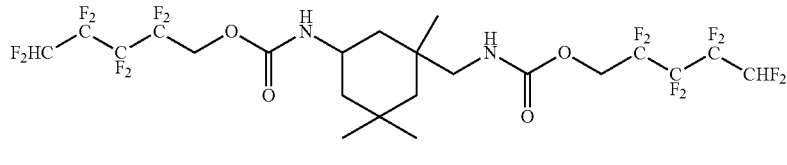

IPDC-4

(19)

The present invention provides a method of producing an isocyanate compound, which comprises:

a step of producing a carbamate compound represented by formula (3), by the production method of a carbamate compound of the present invention; and a step of producing an isocyanate compound represented by formula (20) from the obtained carbamate compound without using a catalyst.

[Chem. 20]

(20)

wherein, A represents a divalent aliphatic hydrocarbon group, a divalent alicyclic hydrocarbon group or a divalent aromatic-aliphatic hydrocarbon group Advantageous Effect of the Invention According to the production method of a carbamate compound of the invention, a carbamate compound can be produced with using neither phosgene nor a catalyst.

The carbamate compound obtained by the production method of a carbamate compound of the invention can be converted into an isocyanate compound without using a catalyst.

According to the production method of an isocyanate compound of the invention, an isocyanate compound can be produced from a carbonic diester compound and a diamine compound, via a carbamate compound with using neither phosgene nor a catalyst.

MODE FOR CARRYING OUT THE INVENTION

Figure 1:
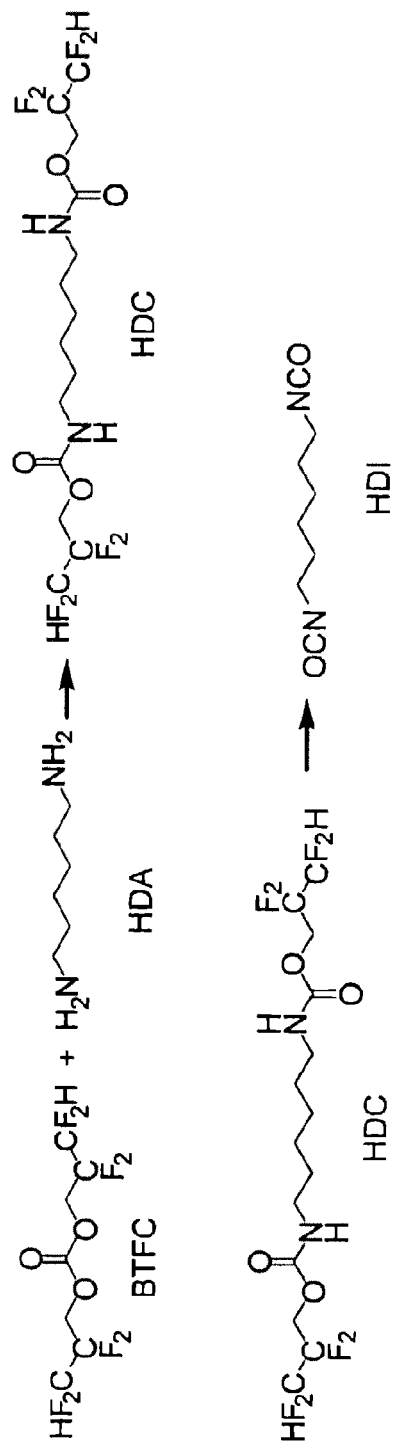
FIG. 1 is a drawing showing a reaction scheme in an example of the invention.

According to this specification, the compound represented by formula (1) is referred to as compound (1). The compounds represented by other formulae are also referred to in the same manner.

According to this specification, the term "fluorine-containing compound" means a compound having a fluorine atom. Also, the term "fluorine-containing group" means a group having a fluorine atom.

According to this specification, the term "polyfluoroalkyl group" means a group in which a part of hydrogen atoms (two or more) of an alkyl group is substituted by fluorine atoms, and the term "perfluoroalkyl group" means a group in which all of the hydrogen atoms of an alkyl group are substituted by fluorine atoms.

According to this specification, the term "fluorine atom on a carbon atom" means a fluorine atom directly bonded to the carbon atom, and the phrase "having no fluorine atom on a carbon atom" means that a fluorine atom directly bonded to the carbon atom is not present.

<Compound (1): Fluorine-Containing Carbonic Diester Compound>

R of formula (1) is a monovalent fluorine-containing aliphatic hydrocarbon group. The two R groups in one molecule are the same group.

The fluorine-containing aliphatic hydrocarbon group as R may contain an ethereal oxygen atom. It may be a straight or branched chain. It may have a substituent group other than fluorine atom. The substituent group is preferably a halogen atom (however, excluding fluorine atom).

The fluorine-containing aliphatic hydrocarbon group is preferably a polyfluoroalkyl group having from 2 to 10 carbon atoms which has no fluorine atom on the α-position carbon atom bonded to the oxygen atom (—O—) of the carbonate bond (—O—C(O)—O—), and is more preferably a polyfluoroalkyl group having from 2 to 5 carbon atoms which has no fluorine atom on the α-position carbon atom. The polyfluoroalkyl group may have an ethereal oxygen atom.

The alkyl group of the polyfluoroalkyl group having from 2 to 10 carbon atoms is preferably ethyl group, n-propyl group, i-propyl group, n-butyl group, t-butyl group or n-pentyl group, and the alkyl group of the polyfluoroalkyl group having an ethereal oxygen atom is preferably (ethoxy (ethoxy))ethyl group, (ethoxy(ethoxy(ethoxy)))ethyl group, (propoxy)propyl group or (propoxy(propoxy))propyl group.

It is preferred that R of formula (1) has no fluorine atom on the α-position carbon atom bonded to the oxygen atom of the carbonate bond and has two or more groups, in total, of at least one member selected from the group consisting of a fluorine atom, a polyfluoroalkyl group and a perfluoroalkyl group bonded to the β-position carbon atom adjacent to the α-position. Each of the polyfluoroalkyl group and perfluoroalkyl group may have an ethereal oxygen atom.

It is preferred that the α-position carbon atom has no fluorine atom thereon from the viewpoint that stability of the compound (1) and stability of the alcohol by-produced by the reaction of the compound (1) and compound (2) (carbamate forming reaction) are good and generation of hydrogen fluoride by their decomposition is suppressed.

In addition, it is preferred that two or more groups, in total, of fluorine atom, polyfluoroalkyl group and/or perfluoroalkyl group are bonded to the β-position carbon atom, from the viewpoint that activity of the oxygen atom of the carbonate bond becomes high due to electron attractive property of the fluorine atom, polyfluoroalkyl group and/or perfluoroalkyl group. When activity of the oxygen atom becomes high, it facilitates the progress of the carbamate forming reaction of the compound (1) with compound (2) and the isocyanate forming reaction by the dealcoholization reaction of the compound (3), in the absence of a catalyst.

Preferred examples of the fluorine-containing aliphatic hydrocarbon group as R include 2,2,3,3-tetrafluoro-n-propyl group, 2,2,3,3,3-pentafluoro-n-propyl group, 1,1,1,3,3,3-hexafluoro-1-propyl group, 2,2,3,3,4,4,5,5-octafluoro-n-pentyl group, 2,2,3,3,4,4,4-hexafluoro-n-butyl group, 2,2,2-trifluoroethyl group, 2,2-difluoroethyl group, 2,2-difluoro-2-(1,1,2,2-tetrafluoro-2-(pentafluoroethoxy)ethoxy)ethyl group ($CF_3CF_2OCF_2CF_2OCF_2CH_2$—), 2,2-difluoro-2-(tetrafluoro-2-(tetrafluoro-2-(pentafluoroethoxy)ethoxy) ethoxy)ethyl group ($CF_3CF_2OCF_2CF_2OCF_2CF_2OCF_2CH_2$—), 2,3,3,3-tetrafluoro-2-(1,1,2,3,3,3-hexafluoro-2-(1,1,2,2,3,3,3-heptafluoropropoxy)propoxy)-1-propyl group ($CF_3CF_2CF_2OCF(CF_3)CF_2OCF(CF_3)CH_2$—) and 2,3,3,3-tetrafluoro-2-(1,1,2,2,3,3,3-heptafluoropropoxy)-1-propyl group ($CF_3CF_2CF_2OCF(CF_3)CH_2$—).

Of these, 2,2,3,3-tetrafluoro-n-propyl group, 2,2,3,3,3-pentafluoro-n-propyl group, 1,1,1,3,3,3-hexafluoro-1-propyl group, 2,2,3,3,4,4,5,5-octafluoro-n-pentyl group, 2,2,3,4,4,4-hexafluoro-n-butyl group or 2,2,2-trifluoroethyl group is particularly preferable from the viewpoint of versatility.

The compound (1) can be produced by the production method which is described below.

<Compound (2): Non-Aromatic Diamine Compound>

A of formula (2) is any one of a divalent aliphatic hydrocarbon group, a divalent alicyclic hydrocarbon group and a divalent aromatic-aliphatic hydrocarbon group. The compound (2) has two primary amino groups. The divalent aromatic-aliphatic hydrocarbon group means a group having an aromatic ring and two alkylene groups directly bonded to the carbon atoms which constitute the aromatic ring, and the two amino groups of compound (2) are respectively bonded to the two alkylene groups. That is, the compound (2) does not have an amino group directly bonded to the aromatic ring.

A of formula (2) may have a bond or functional group which is thermally-stable at the temperature of the isocyanate forming reaction step and hardly reacts with isocyanate group, wherein the bond or functional group contains such as an ether bond, a thioether bond, an ester bond, a sulfone group, a carbonyl group, and a halogen atom.

When A is a divalent aliphatic hydrocarbon group, the compound (2) is an aliphatic diamine. The number of carbon atoms of the aliphatic hydrocarbon group as A is preferably from 2 to 40, and more preferably from 2 to 20.

The aliphatic diamine includes, for example, 1,2-diaminoethane, 1,3-diaminopropane, 1,4-diaminobutane, 1,5-diaminopentane, 1,6-diaminohexane (also referred to as 1,6-hexamethylenediamine), 1,7-diaminoheptane, 1,8-diaminooctane, 1,9-diaminononane, 1,10-diaminodecane, 1,12-diaminododecane, 2,2,4-trimethylhexamethylenediamine, 2,4,4-trimethylhexamethylenediamine, tetramethylenediamine, and 1,2-bis(aminoethylthio)ethane.

In addition, also included in the aliphatic diamine are, for example, an amino group-containing polyoxyalkylene compound such as polyoxypropylene diamine, and an amino group-containing polysiloxane compound.

When A is a divalent alicyclic hydrocarbon group, the compound (2) is an alicyclic diamine. The number of carbon atoms of the alicyclic hydrocarbon group as A is preferably from 4 to 40, and more preferably from 4 to 20.

The alicyclic diamine includes, for example, diaminocyclobutane, isophoronediamine (3-aminomethyl-3,5,5-trimethylcyclohexylamine), 1,2-diaminocyclohexane, 1,3-diaminocyclohexane, 1,4-diaminocyclohexane, 1,3-bis (aminomethyl)cyclohexane, 1,4-bis(aminomethyl) cyclohexane, 4,4'-diamino(dicyclohexylmethane), 2,5-bis (aminomethyl)bicyclo[2,2,1]heptane, 2,6-bis(aminomethyl) bicyclo[2,2,1]heptane, hydrogenerated 2,4-toluenediamine, and hydrogenerated 2,6-toluenediamine.

When A is a divalent aromatic-aliphatic hydrocarbon group, the compound (2) is an aromatic-aliphatic diamine. The number of carbon atoms of the aromatic-aliphatic hydrocarbon group as A is preferably from 8 to 40, more preferably from 8 to 20. The number of carbon atoms of the alkylene group presenting between the aromatic ring and the amino group is preferably from 1 to 10, and more preferably from 1 to 5. It is preferable that the alkylene group is straight chain.

The aromatic-aliphatic diamine includes, for example, 1,3-bis(aminomethyl)benzene, and 1,4-bis(aminomethyl)benzene.

Of these, particularly from the viewpoint that an industrially useful diisocyanate can be obtained, for example, 1,6-hexamethylenediamine, isophoronediamine, 1,3-bis(aminomethyl)cyclohexane, 1,4-bis(aminomethyl)cyclohexane, 4,4'-diamino(dicyclohexylmethane), 2,5-bis(aminomethyl) bicyclo[2,2,1]heptane, 2,6-bis(aminomethyl)bicyclo[2,2,1] heptane, 1,3-bis(aminomethyl)benzene or 1,4-bis(aminomethyl)benzene is suitably used as the compound (2). From the viewpoint of reactivity, 1,6-hexamethylenediamine or 1,3-bis (aminomethyl)benzene is particularly preferable.

The compound (2) can be produced by a conventionally known production method and can also be available from commercial items.

<Compounds (3) to (19): Carbamate Compounds>

Compound (3) is a reaction product of the compound (1) and compound (2). R of formula (3) is the R derived from compound (1) and A is the A derived from compound (2). The compound (3) provides diisocyanate compound by thermally decomposing easily even under the absence of a catalyst. That is, the compound (3) can be used as an intermediate in producing a diisocyanate compound (20) from the compound (1) and compound (2). In addition, the compound (3) can also be used as blocked diisocyanate compound.

Of the compound (3), compounds (4) to (20) are preferable from the view points that the balance of stability and reactivity is particularly proper and that a high-value-added isocyanate can be obtained.

The compound (4) is a reaction product obtained by reacting a compound (1) in which R is 2,2,3,3-tetrafluoro-n-propyl group with 1,3-bis(aminomethyl)benzene which is the compound (2), in the absence of a catalyst.

The compound (5) is a reaction product obtained by reacting a compound (1) in which R is 2,2,2-trifluoroethyl group with 1,3-bis(aminomethyl)benzene which is the compound (2), in the absence of a catalyst.

The compound (6) is a reaction product obtained by reacting a compound (1) in which R is 2,2,3,3,3-pentafluoro-n-propyl group with 1,3-bis(aminomethyl)benzene which is the compound (2), in the absence of a catalyst.

The compound (7) is a reaction product obtained by reacting a compound (1) in which R is 2,2,3,3,4,4,5,5-octafluoro-n-pentyl group with 1,3-bis(aminomethyl)benzene which is the compound (2), in the absence of a catalyst.

The compound (8) is a reaction product obtained by reacting a compound (1) in which R is 2,2,3,3-tetrafluoro-n-propyl group with 1,3-bis(aminomethyl)cyclohexane which is the compound (2), in the absence of a catalyst.

The compound (9) is a reaction product obtained by reacting a compound (1) in which R is 2,2,2-trifluoroethyl group with 1,3-bis(aminomethyl)cyclohexane which is the compound (2), in the absence of a catalyst.

The compound (10) is a reaction product obtained by reacting a compound (1) in which R is 2,2,3,3,3-pentafluoro-n-propyl group with 1,3-bis(aminomethyl)cyclohexane which is the compound (2), in the absence of a catalyst.

The compound (11) is a reaction product obtained by reacting a compound (1) in which R is 2,2,3,3,4,4,5,5-octafluoro-n-pentyl group with 1,3-bis(aminomethyl)cyclohexane which is the compound (2), in the absence of a catalyst.

The compound (12) is a reaction product obtained by reacting a compound (1) in which R is 2,2,3,3-tetrafluoro-n-propyl group with 4,4'-diamino(dicyclohexylmethane) which is the compound (2), in the absence of a catalyst.

The compound (13) is a reaction product obtained by reacting a compound (1) in which R is 2,2,2-trifluoroethyl group with 4,4'-diamino(dicyclohexylmethane) which is the compound (2), in the absence of a catalyst.

The compound (14) is a reaction product obtained by reacting a compound (1) in which R is 2,2,3,3,3-pentafluoro-n-propyl group with 4,4'-diamino(dicyclohexylmethane) which is the compound (2), in the absence of a catalyst.

The compound (15) is a reaction product obtained by reacting a compound (1) in which R is 2,2,3,3,4,4,5,5-octafluoro-n-pentyl group with 4,4'-diamino(dicyclohexylmethane) which is the compound (2), in the absence of a catalyst.

The compound (16) is a reaction product obtained by reacting a compound (1) in which R is 2,2,3,3-tetrafluoro-n-propyl group with 3-aminomethyl-3,5,5-trimethylcyclohexylamine which is the compound (2), in the absence of a catalyst.

The compound (17) is a reaction product obtained by reacting a compound (1) in which R is 2,2,2-trifluoroethyl group with 3-aminomethyl-3,5,5-trimethylcyclohexylamine which is the compound (2), in the absence of a catalyst.

The compound (18) is a reaction product obtained by reacting a compound (1) in which R is 2,2,3,3,3-pentafluoro-n-propyl group with 3-aminomethyl-3,5,5-trimethylcyclohexylamine which is the compound (2), in the absence of a catalyst.

The compound (19) is a reaction product obtained by reacting a compound (1) in which R is 2,2,3,3,4,4,5,5-octafluoro-n-pentyl group with 3-aminomethyl-3,5,5-trimethylcyclohexylamine which is the compound (2), in the absence of a catalyst.

<Compound (20): Isocyanate Compound>

The compound (20) is a diisocyanate compound obtained by thermally decomposing the compound (3). A of formula (20) is the A derived from the compound (2).

<Production Method of Compound (1)>

The compound (1) can be produced for example by the following method, in a high yield without using phosgene. In this connection, it is not limited to this method.

That is, the compound (1) is obtained by reacting a compound (21) with a fluorine-containing aliphatic alcohol represented by R—OH(R is the same as the R of formula (1)), in the presence of a catalyst as necessary.

[Chem. 21]

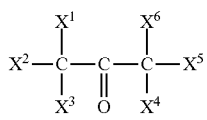

(21)

Each of $X^1$ to $X^3$ of formula (21) represents a hydrogen atom or a halogen atom, and at least one of the $X^1$ to $X^3$ is a halogen atom. Each of $X^4$ to $X^6$ represents a hydrogen atom or a halogen atom, and at least one of the $X^4$ to $X^6$ is a halogen atom.

It is preferable that each of the $X^1$ to $X^6$ is a halogen atom, more preferably fluorine atom or chlorine atom. Hexachloroacetone is most preferable as the compound (21) from the viewpoint that industrially useful chloroform can also be produced in a high yield as a by-product and in view of reactivity.

The catalyst includes an alkali metal, an alkaline earth metal; an alkali metal hydride, an alkaline earth metal hydride; an alkali metal hydroxide, an alkaline earth metal hydroxide; a phase-transfer catalyst; a halogen salt of an alkali metal, a halogen salt of an alkaline earth metal, a halogen salt of ammonium; an ion exchange resin; a compound of at least one metal selected from the group consisting of tin, titanium, aluminum, tungsten, molybdenum, zirconium and zinc; and at least one substance selected from the group consisting of ester exchange reaction catalysts.

From the viewpoints of easy handling, reaction activity and selectivity of the target substance in industrially using it, a halogen salt is preferable. Preferred as the halogen salt is at least one kind selected from the group consisting of a halogen salt of an alkali metal; a halogen salt of an alkaline earth metal; a halogen salt of ammonium, a halogen atom of a quaternary ammonium and an ion exchange resin having a halogen salt structure.

In addition, the catalytic activity can be improved when a co-catalyst is used together with the catalyst. Preferred as the co-catalyst is a solid acid catalyst selected from the group consisting of a metal oxide having an acid site, a heteropolyacid and a cation exchange resin.

Preferred as the metal oxide having an acid site is at least one species selected from the group consisting of cerium oxide ($CeO_2/Ce_2O_3$), silica alumina ($SiO_2.Al_2O_3$), γ-alumina ($Al_2O_3$), silica magnesia ($SiO_2.MgO$), zirconia ($ZrO_2$), silica zirconia ($SiO_2.ZrO_2$), $ZnO.ZrO_2$ and $Al_2O_3.B_2O_3$.

These catalyst and co-catalyst can be successfully separated and removed after the reaction by a conventional technique such as filtration, distillation or water washing, or a technique in combination thereof.

<Production Method of Compound (3)>

According to the invention, the compound (3) is obtained by reacting the compound (1) and compound (2) without using a catalyst. It is preferable to react from 2 moles to 20 moles, more preferably from 2 moles to 10 moles, of the compound (1) with 1 mole of the compound (2). The R—OH is by-produced by this reaction.

This reaction may be carried out under no solvent which does not use a solvent, or in a solvent. It is preferable to carry out the reaction under no solvent from the viewpoints that the compound (1) which is used in an excess amount acts by itself as a solvent, that there is a case of lowering the reaction activity due to dilution by use of the solvent, and that removal of the solvent is not necessary. In addition, the reaction may be carried out under normal pressure or under a pressurized condition (e.g., approximately from 0.11 MPa to 0.5 MPa).

Since the decomposition reaction is accelerated when the reaction temperature is too high and the material and formed product are solidified when it is too low, it is preferable to set the reaction temperature within such a range that these inconvenient phenomena do not occur. For example, it is preferably from −10° C. to 250° C., and more preferably from 0° C. to 150° C.

Since efficiency of the apparatus in the production process becomes poor when the reaction time is too long and there is a possibility that thermorunaway caused by an exothermic action becomes uncontrollable when the reaction is carried out within a short period of time, it is preferable to set the reaction time within such a range that these inconvenient phenomena do not occur. For example, a period of from 0.1 hour to 40 hours is preferable, and from 0.5 hour to 20 hours is more preferable. In this connection, the reaction time is not limited to this when kind of the reaction solvent and selectivity are seriously considered.

The by-produced R—OH (fluorine-containing aliphatic alcohol) can be evaporated by heating or heating under a reduced pressure. The heating condition under a reduced pressure can be optionally set within such a range that it does not exert a bad influence upon the compound (3) as the target substance. For example, it is preferable to carry out the process under conditions of from 50° C. to 160° C. and from 135 Torr to 100 Torr (approximately from $18.0 \times 10^3$ Pa to $13.3 \times 10^3$ Pa).

When a solvent is used, the solvent that satisfies the following condition (i) is preferable.

Condition (i): it does not substantially react with the compound (3).

The phrase "does not substantially react with compound (3)" means that it does not react at all with the —N(H)—C(O)—O—R group of compound (3), or even when reacts therewith, it is such a slight level that it does not spoil the effect of the invention.

Examples of the group capable of reacting with the —N(H)—C(O)—O—R group of compound (3), include aldehyde group, acetoacetyl group, and an active hydrogen-containing group. Accordingly, a solvent that does not have these groups is preferable as the solvent.

The aforementioned active hydrogen includes a hydrogen atom directly bonded to a hetero atom; a hydrogen atom bonded to the carbon atom adjacent to an electron attractive group (α-hydrogen atom); a hydrogen atom constituting a substitution aromatic substance; and a hydrogen atom constituting a functional group such as an aldehyde and a carboxylic acid.

The aforementioned hydrogen atom directly bonded to a hetero atom includes a hydrogen atom constituting a functional group such as —$NH_2$ group, —CONH group, —OH group, or —SH group.

The aforementioned hydrogen atom bonded to the carbon atom adjacent to an electron attractive group includes the α-position hydrogen atom of a carbonyl compound.

<Production Method of Compound (20)>

After obtaining the compound (3) by reacting the compound (1) and compound (2) in the absence of a catalyst, the excess materials and by-products are evaporated as necessary, and the compound (20) is produced from the compound (3) without using a catalyst. Illustratively, the compound (20) is obtained by subjecting the compound (3) to thermal decomposition. Since this reaction is a dealcoholization reaction and by-produces R—OH, it is preferable to carry out the reaction while evaporating the by-produced R—OH.

This reaction may be carried out under no solvent which does not use a solvent, or in a solvent. In addition, it may be carried out under normal pressure or may be carried out under a condition of a reduced pressure (e.g., approximately from 20 Torr to 6 Torr (about from 2,660 Pa to about 800 Pa)).

Since decomposition of the target products (isocyanate compounds) and formation of polymers occurs when the reaction temperature is too high and the reaction does not progress when it is too low, it is preferable to set the reaction temperature within such a range that these inconvenient phenomena do not occur. For example, it is preferably from 100° C. to 350° C., more preferably from 150° C. to 250° C.

Efficiency of the apparatus in the production process becomes poor when the reaction time is too long. For example, 100 hours or less is preferable and 40 hours or less is more preferable. In this connection, the reaction time is not limited to this when kind of the reaction solvent and selectivity are seriously considered and also varies depending on the reaction conditions. There is a case in which selectivity of the target substance can be improved when the reaction is carried out at a high temperature for a short period of time in order to inhibit decomposition of the product, using a continuous reaction process or the like.

When a solvent is used, the solvent that satisfies the following condition (ii) is preferable.

Condition (ii): it does not substantially react with isocyanate group of the compound (20), namely, it does not have the active hydrogen described in the above-mentioned condition (i). Use of a solvent which satisfies both of the conditions (i) and (ii) is preferable because the step of obtaining the compound (3) from the compound (1) and compound (2) and the step of obtaining the compound (20) from the compound (3) can be continuously carried out.

Examples of the solvent that satisfies both of the conditions (i) and (ii), preferably, includes illustratively at least one substance selected from the group consisting of ethers which do not have active hydrogen (such as diglyme, triglyme, diethyl ether or dibutyl ether), esters (such as ethyl acetate or butyl acetate), ketones (such as acetone, diethyl ketone or methyl isobutyl ketone), aliphatic hydrocarbons (such as hexane, heptane or octane), aromatic hydrocarbons (such as benzene, toluene, xylene, or ethylbenzene) and halogenated hydrocarbons (such as chloroform, carbon tetrachloride, dichloroethylene, or trichloroethylene).

In addition, the solvent may have two or more bonds, groups and/or atoms in 1 molecule, selected from the group consisting of an ether bond, an ester bond, a ketone, an aliphatic hydrocarbon group, an aromatic hydrocarbon group and a halogen atom. Such a solvent includes, for example, ester ethers (such as ethylene glycol monoethyl ether monoacetate).

According to the production method of the invention, the compound (3) can be produced from the compound (1) and compound (2) in a high yield without using a catalyst, and the compound (20) can be further produced from the compound (3) in a high yield without using a catalyst.

For example, yield of the compound (3) based on the compound (2) as a diamine compound can realize a level of 80% by mol or more. Yield of the compound (20) based on the compound (3) as a carbamate compound can realize a level of 50% by mol or more.

In addition, since a catalyst is not used at all, the formed product (compound (3) or compound (20)) can be easily isolated and the target substance can be easily obtained with a high purity.

As described above, it has been conventionally considered that a catalyst is necessary for the production of fluorine-containing carbamate compounds, and actually, the patent reference 4 describes a case in which an aromatic fluorine-containing dicarbamate compound was not formed when a catalyst was not used. In addition, as there is a description of "the amines which can be used in the context of the present invention are aliphatic or aromatic amines . . . " in paragraph [0030] of the patent reference 4, it has been considered that the reaction occurs in the same manner in the case of either an aliphatic amine or an aromatic amine.

However, to our surprise, according to the invention, when a non-aromatic diamine compound which does not have an amino group directly bonded to an aromatic ring is used as a diamine compound to be reacted with a fluorine-containing carbonic diester compound of the compound (1), a fluorine-containing dicarbamate compound can be obtained through their reaction even in the absence of a catalyst. What is more, the thus obtained fluorine-containing dicarbamate compound can be converted into a diisocyanate compound even in the absence of a catalyst.

Though the reason for this is not clear, it is considered that there is a great difference in reactivity between the amino group directly bonded to an aromatic ring and the amino group not bonded to the aromatic ring, upon reacting with the fluorine-containing carbonic diester compound.

EXAMPLES

The following describes the invention further in detail using examples, though the invention is not limited to these examples. In the following, the conversion ratio is "% by mol", the purity is "area % in a gas chromatography analysis" and the yield is "% by mol".

Synthesis Example 1

A 500 mL capacity glass reactor equipped with a stirrer, a 20° C. reflux condenser and a distillation line was charged with 262 g (0.99 mol) of hexachloroacetone (chemical agent of Tokyo Chemical Industry Co., Ltd.: Product Number of H0335), 392 g (2.97 mol) of 2,2,3,3-tetrafluoro-1-propanol (chemical agent of SynQuest Laboratories: Product Number of 2101-3-10), and 4 g of anhydrous potassium fluoride (manufactured by Yellow River Fine Chemical), gradually heated while stirring, and then the mixture was subjected to reaction at the inner temperature of 100° C.

The reaction was carried out for 10 hours while distilling off chloroform generated during the reaction through the distillation line. After completion of the reaction, the fraction distilled through the distillation line and the crude reaction solution remained in the reactor were collected, and thereby obtaining 645 g (collection rate: 98%) of crude collected solution. The crude collected solution was distilled under a reduced pressure to separate from the catalyst used, and simultaneously, 100 g of bis(2,2,3,3-tetrafluoropropyl) carbonate (to be referred to as "BTFC" hereinafter) was obtained in purity of 99%.

Synthesis Example 2

The reaction and distillation were carried out in the same manner as Synthesis Example 1 except for using 297 g (2.97 mol) of 2,2,2-trifluoroethanol (chemical agent of SynQuest Laboratories: Product Number of 2101-3-03), thereby obtaining 80 g of bis(2,2,2-trifluoroethyl) carbonate (to be referred to as "BTrFC" hereinafter) in purity of 99%.

Synthesis Example 3

The reaction and distillation were carried out in the same manner as Synthesis Example 1 except for using 446 g (2.97 mol) of 2,2,3,3,3-pentafluoro-1-propanol (chemical agent of SynQuest Laboratories: Product Number of 2101-3-08), thereby obtaining 110 g of bis(2,2,3,3,3-pentafluoropropyl) carbonate (to be referred to as "BPFC" hereinafter) in purity of 99%.

Synthesis Example 4

The reaction and distillation were carried out in the same manner as Synthesis Example 1 except for using 689 g (2.97 mol) of 2,2,3,3,4,4,5,5-octafluoro-1-pentanol (chemical agent of SynQuest Laboratories: Product Number of 2101-3-15), thereby obtaining 150 g of bis(2,2,3,3,4,4,5,5-octafluoropentyl) carbonate (to be referred to as "BOFC" hereinafter) in purity of 99%.

Example 1

Synthesis of Aliphatic Diisocyanate Compound

By the reaction shown in FIG. 1, 1,6-hexamethylene diisocyanate (to be referred to as "HDI" hereinafter) was synthesized.

That is, a 50 mL capacity glass reactor equipped with a stirrer, a 20° C. reflux condenser and a distillation line was charged with 8.78 g (0.0756 mol) of 1,6-hexamethylenediamine (chemical agent of KANTO CHEMICAL CO., INC.: Product Number of 18033-10, and to be referred to as "HDA" hereinafter) and then heated to 70° C. while stirring. To this was added dropwise 44.79 g (0.1544 mol) of bis(2,2,3,3-tetrafluoropropyl) carbonate (to be referred to as "BTFC" hereinafter) synthesized in the above Synthesis Example 1. In this case, the dropwise addition rate was adjusted to such a manner that increase of the inner temperature ($\Delta T$) becomes 10° C. or lower. After completion of the dropwise addition, the reaction was carried out while stirring at 70° C. for 1 hour.

The crude liquid after completion of the reaction was cooled to room temperature, and then a portion of the crude liquid was collected and its composition was analyzed by a $^1$H-NMR. The analysis results are shown in the following. From the analytical results, it was confirmed that unreacted HDA was completely disappeared (HDA conversion ratio 100%) and that 1,6-hexamethylene bis(2,2,3,3-tetrafluoropropyl carbamate) (to be referred to as "HDC" hereinafter) generated as the main product. Yield of the HDC (gas chromatography purity 99%) based on HDA was 99.4% by mol.

HDC: $^1$H-NMR δ: 1.267 (4H, s); 1.445 (4H, s); 3.119 (4H, m, J=6.6); 4.385 (4H, t, J=13.2); 5.783 (2H, tt, J=3.9, 53.1)

From the crude liquid obtained in the above, the 2,2,3,3-tetrafluoropropanol (to be referred to as TFPO hereinafter) by-produced by the reaction of HDA and BTFC and the unreacted BTFC were evaporated by heating under a reduced pressure. The heating under a reduced pressure was carried out under a condition of 100° C. and 135 Torr (about $18.0 \times 10^3$ Pa) for 1 hour to thereby evaporate TFPO firstly, and then carried out under a condition of 160° C. and 100 Torr (about $13.3 \times 10^3$ Pa) for 1 hour to thereby evaporate BTFC.

Subsequently, the liquid in the reactor was heated to 200° C. and decompressed until bubbling started (940 Pa). The bubbling becomes a measure for the generation of TFPO by thermal decomposition of HDC.

Under this condition, the reaction was carried out for 14 hours while recovering the TFPO generated by the reaction by using a dry ice trap. The dry ice trap is arranged in the middle of a decompression line connected to the distillation line of the reflux condenser. HDI as the target substance was recovered by a receiver arranged on the distillation line.

The presence of HDI was confirmed by carrying out a gas chromatography analysis of a portion of the crude liquid (6.04 g) recovered in the receiver and comparing with a standard article. Yield of the HDI (gas chromatography purity 95%) based on HDC was 64% by mol.

Example 2

Synthesis of Aromatic-Aliphatic Diisocyanate Compound

Figure 2:
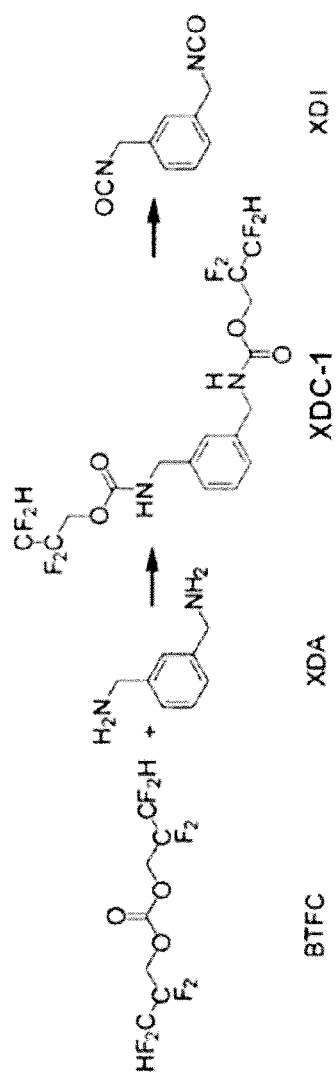
FIG. 2 is a drawing showing a reaction scheme in another example of the invention.

By the reaction shown in FIG. 2, m-xylylene diisocyanate (to be referred to as XDI hereinafter) was synthesized.

That is, a 50 mL capacity glass reactor equipped with a stirrer, a 20° C. reflux condenser and a distillation line was charged with 8.83 g (0.0648 mol) of m-xylenediamine (chemical agent of Tokyo Chemical Industry Co., Ltd.: Product Number of D0127, also called 1,3-bis(aminomethyl)benzene, and to be referred to as "XDA" hereinafter) and then heated to 50° C. while stirring. To this was added dropwise 47.63 g (0.1642 mol) of BTFC synthesized in the above Synthesis Example 1. In this case, the dropwise addition rate was adjusted to such a manner that increase of the inner temperature ($\Delta T$) becomes 10° C. or lower. After completion of the dropwise addition, the reaction was carried out while stirring at 50° C. for 1 hour.

The crude liquid after completion of the reaction was cooled to room temperature, and then a portion of the crude liquid was collected and its composition was analyzed by a $^1$H-NMR. The analysis results are shown in the following. From the analytical results, it was confirmed that unreacted XDA was completely disappeared (XDA conversion ratio 100%) and that m-xylylene bis(2,2,3,3-tetrafluoropropyl carbamate) (to be referred to as XDC-1 hereinafter) generated as the main product. Yield of the XDC-1 (gas chromatography purity 99%) based on XDA was 99.4% by mol.

XDC-1: $^1$H-NMR δ: 4.357 (4H, d, J=6 Hz); 4.492 (4H, t, J=12.9 Hz); 5.329 (2H, bs); 5.851 (2H, tt, J=3.9, 53.1); 7.179-7.346 (4H, m)

Structural assignment of the thus obtained XDC-1 was analyzed by $^{19}$F-NMR and GC-Mass analyses. The analyses results are shown in the following.

XDC-1: $^{19}$F-NMR δ: −137.936 (4F, d, J=31.2 Hz); −124.506 (4F, m)

XDC-1: MS m/z: 91 ($PhCH_2$); 118 ($CH_2PhCH_2N$); 146 ($CH_2NHPhCH_2NHC$); 161 ($CHPhCH_2NC(=O)O$); 277 ($CHPhCH_2NHC(=O)OCH_2CF_2CF_2H$)

From the crude liquid obtained in the above, the TFPO by-produced by the reaction of XDA and BTFC and the unreacted BTFC were evaporated by heating under a reduced pressure. The heating under a reduced pressure was carried out under the same conditions as in Example 1.

Subsequently, the liquid in the reactor was heated to 200° C. and decompressed until bubbling started (940 Pa). The bubbling becomes a measure for the generation of TFPO by thermal decomposition of XDC-1.

Under this condition, the reaction was carried out for 14 hours while recovering the TFPO generated by the reaction in the same manner as in Example 1. XDI as the target substance was recovered by a receiver arranged on the distillation line.

The presence of XDI was confirmed by carrying out a gas chromatography analysis of a portion of the crude liquid (6.23 g) recovered in the receiver and comparing with a standard article. Yield of the XDI (gas chromatography purity 90%) based on XDC-1 was 50% by mol.

Example 3

Synthesis of aromatic-aliphatic diisocyanate Compound: Synthesis of m-xylylene dicarbamate (XDC-1)

A 50 mL capacity glass reactor equipped with a stirrer, a 20° C. reflux condenser and a distillation line was charged with 8.83 g (0.0648 mol) of m-xylenediamine (chemical agent of Tokyo Chemical Industry Co., Ltd.: Product Number of D0127, and to be referred to as "XDA" hereinafter) and then heated to 50° C. while stirring. Next, 47.63 g (0.1642 mol) of bis(2,2,3,3-tetrafluoropropyl) carbonate (to be referred to as "BTFC" hereinafter) synthesized in the above Synthesis Example 1 was added dropwise thereto while adjusting the rate in such a manner that increase of the inner temperature ($\Delta T$) becomes 10° C. or lower. After completion of the dropwise addition, the reaction was carried out while stirring at 50° C. for 1 hour. After completion of the reaction, the crude liquid was cooled to room temperature, and then a portion of the crude liquid was collected and its composition was analyzed by a $^1$H-NMR. As a result, it was confirmed that unreacted XDA was completely disappeared (XDA conversion ratio 100%) and that m-xylylene bis(2,2,3,3-tetrafluoropropyl carbamate) (to be referred to as XDC-1 hereinafter) was generated as the main product (XDA base yield 99.4%). XDC-1 as the product was obtained in a yield of 99.4%. Structural assignment of the product XDC-1 was carried out by $^{19}$F-NMR and GC-Mass analyses as well as $^1$H-NMR. Analytical Results of mass fragments of XDC-1, $^1$H-NMR and $^{19}$F-NMR were shown in the following.

XDC-1: $^1$H-NMR δ: 4.357 (4H, d, J=6 Hz); 4.492 (4H, t, J=12.9 Hz); 5.329 (2H, bs); 5.851 (2H, tt, J=3.9, 53.1); 7.179-7.346 (4H, m)

XDC-1: $^{19}$F-NMR δ: −137.936 (4F, d, J=31.2 Hz); −124.506 (4F, m)

XDC-1: MS m/z: 91 (PhCH$_2$); 118 (CH$_2$PhCH$_2$N); 146 (CH$_2$NHPhCH$_2$NHC); 161 (CHPhCH$_2$NC(=O)O); 277 (CHPhCH$_2$NHC(=O)OCH$_2$CF$_2$CF$_2$H)

[Chem. 22]

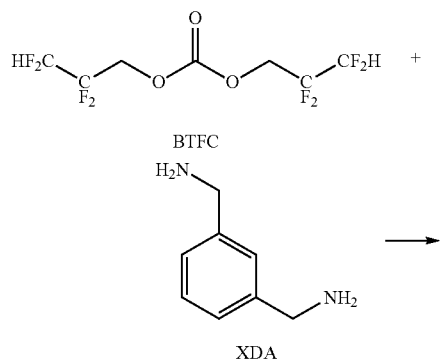

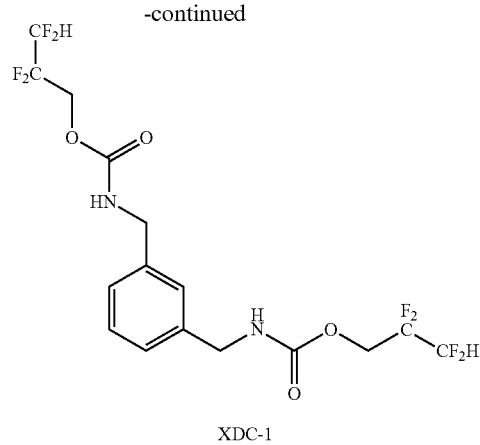

XDC-1

Synthesis of m-xylylene diisocyanate (XDI)

From the crude liquid obtained in the above, the 2,2,3,3-tetrafluoropropanol (to be referred to as TFPO hereinafter) by-produced by the reaction of XDA and BTFC and the unreacted BTFC were evaporated by heating under a reduced pressure. The heating under a reduced pressure was carried out under a condition of 100° C. and 135 Torr (about 18.0×10$^3$ Pa) for 1 hour to thereby evaporate II-PO, and then carried out under a condition of 160° C. and 100 Torr (about 13.3×10$^3$ Pa) for 1 hour to thereby evaporate BTFC. By evaporation of TFPO and unreacted BTFC, 29 g of XDC-1 with 99% of purity could be recovered.

Next, the recovered XDC-1 was introduced into a stainless-steel storage tank (made of SUS-316) kept at 100° C., and the tank was connected to a heat reaction tube via a flow controlling valve kept at 100° C. A stainless-steel tube (SUS-316) having a length of 30 cm and an outer diameter of ⅜ inch and filled with an irregular filler made of stainless-steel (HELI PACK No. 1, manufactured by TO-TOKU ENGINEERING CO., LTD.) up to a 20 cm height was used as the heat reaction tube. XDC-1 was continuously supplied from the upper part of the reactor at a rate of 10 mL/h by adjusting the flow controlling valve, while heating the heat reaction tube with a tube furnace and keeping inside of the reaction tube at a decompression degree of 5 mmHg. A thermal decomposition reaction was carried out while controlling the temperature of the tube furnace at such a level that the temperature of the reactor inlet part became 235° C.±10° C. The reaction products were recovered in a glass recovery container part cooled at room temperature and in a glass trap cooled at −78° C., and analyses of the respectively recovered crude liquids were carried out by a gas chromatography and a high performance liquid chromatography using toluene as the internal standard. The analyses results were shown in Table 1 (conversion ratio and selectivity were calculated as % by mol based on XDC-1).

TABLE 1

| | |
|---|---|
| XDC-1 conversion ratio | 96.0% |
| XDI selectivity | 85.4% |
| XMI (reaction intermediate) | 14.3% |
| Others*) | 0.3% |

*)Others: A mixture of non-volatile oligomer components. An isocyanurate mixture of cyclized trimers by-produced from XDI and XMI The thus recovered reaction crude liquids were introduced into a 50 mL capacity glass flask equipped with a reflux line which was cooled at 20° C., XMI was concentrated by removing XDI and TFPO through their evaporation under a reduced pressure, and then the liquid in the reaction container was heated to 200° C. and decompressed until bubbling started (940 Pa). The reaction was carried out under this condition for 5 hours while recovering the formed product by the recovery container arranged on the reflux line and a dry ice trap arranged between the reflux line and a decompression pump. The reaction products thus recovered in the recovery container was subjected to a gas chromatography analysis and it was confirmed that XDI is recovered as the main product. The intermediate XMI can be converted into XDI with a high yield by introducing it after its recovery again into the thermal decomposition reactor together with the material XDC-1. Therefore, this reaction enables to synthesis XDI in a high yield by the reaction of XDC-1.

A portion of XMI, which was concentrated by removing XDI and TFPO through evaporation of the crude liquid under a reduced pressure, was analyzed by mass spectrometry analysis. From the results, it was confirmed that it has the structure shown in formula C.

XML MS m/z: 51 ($CF_2H$); 91 ($PhCH_2$); 118 (CHPhCHN); 146 (CHPhCHNC(=O)); 161 ($CH_2$NPhCHNC(=O)): 188 ($CH_2$NHC(=O)$OCH_2CF_2CF_2H$); 264 ($PhCH_2$NHC(=O)$OCH_2CF_2CF_2H$); 277 (CHPh$CH_2$NHC(=O)$OCH_2CF_2CF_2H$); 319 (NCO$CH_2$Ph$CH_2$NHC(=O)$OCH_2CF_2CF_2$)

[Chem. 23]

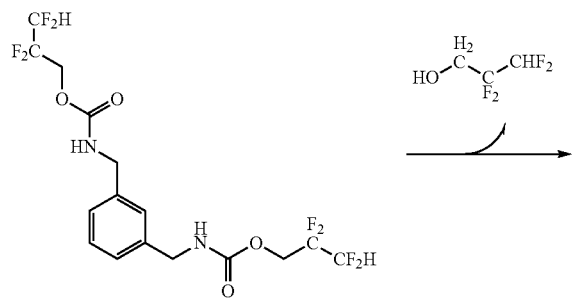

XDC-1

[Chem. 24]

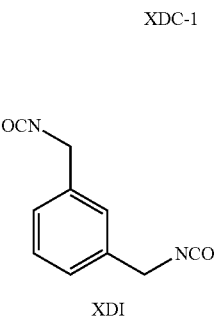

XMI

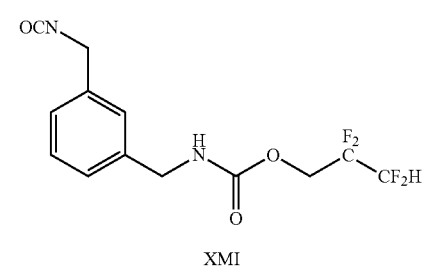

(C)

XMI

Example 4

Synthesis of m-xylylene dicarbamate (XDC-2)

The reaction was carried out in the same manner as Example 3 except for using 37.1 g (0.1642 mol) of bis(2,2,2-trifluoroethyl) carbonate (to be referred to as "BTrFC" hereinafter) synthesized in the above Synthesis Example 2 in place of BTFC, and it was confirmed that m-xylylene bis(2,2,2-trifluoroethyl carbamate) (to be referred to as XDC-2 hereinafter) was generated as the main product (XDA base yield 93.5%). Structural assignment of the product XDC-2 was carried out by $^{19}$F-NMR and GC-Mass analyses as well as $^1$H-NMR. Analytical Results of mass fragments of XDC-2, $^1$H-NMR and $^{19}$F-NMR were shown in the following.

XDC-2: $^1$H-NMR δ: 4.279-4.300 (4H, d, J=6.31 Hz); 4.472-4.589 (4H, q, J=9.01 Hz); 7.179-7.338 (4H, m)

XDC-2: $^{19}$F-NMR δ: −73.802-73.863 (6F, t, J=8.48 Hz)

XDC-2: MS m/z: 91 ($PhCH_2$); 118 ($CH_2PhCH_2N$); 146 (NHCH$_2$PhCH$_2$NHC); 161 (CHPhCH$_2$NC(=O)O); 232 ($CF_3CH_2$OC(=O)NHPh); 246 ($CF_3CH_2$C(=O)NHPhCH$_2$); 261 ($CF_3CH_2$C(=O)NHPhCH$_2$NH); 305 ($CF_3CH_2$OC(=O)NHPhCH$_2$NHC(=O)O)

[Chem. 25]

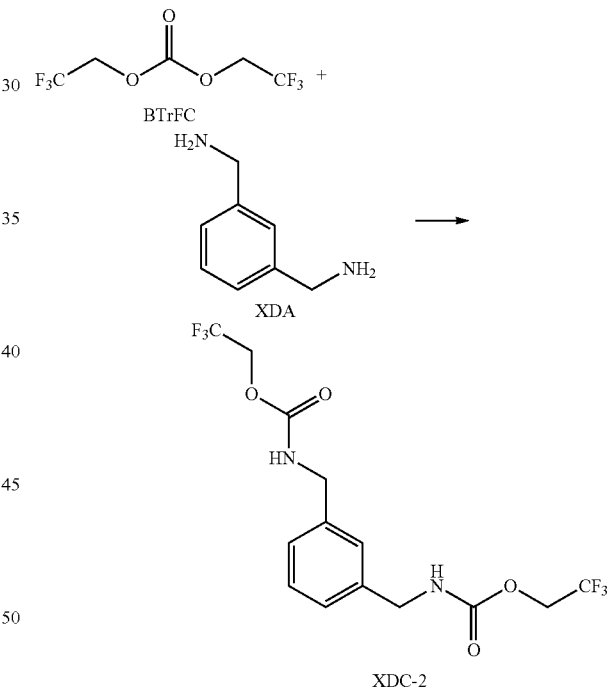

XDC-2

Example 5

Synthesis of m-xylylene dicarbamate (XDC-3)

The reaction was carried out in the same manner as Example 3 except for using 53.5 g (0.1642 mol) of bis(2,2,3,3,3-pentafluoropropyl) carbonate (to be referred to as "BPFC" hereinafter) synthesized in the above Synthesis Example 3 in place of BTFC, and it was confirmed that m-xylylene bis(2,2,3,3,3-pentafluoropropyl carbamate) (to be referred to as XDC-3 hereinafter) was generated as the main product (XDA base yield 96.5%). Structural assignment of the product XDC-3 was carried out by $^{19}$F-NMR and GC-Mass analyses as well as $^1$H-NMR. Analytical Results of mass fragments of XDC-3, $^1$H-NMR and $^{19}$F-NMR were shown in the following.

XDC-3: $^1$H-NMR δ: 4.277-4.298 (4H, d, J=6.31 Hz); 4.589-4.638 (4H, q, J=13.52 Hz); 7.172-7.338 (4H, m)

XDC-3: $^{19}$F-NMR δ: −83.345 (6F, s); −123.137-123.229 (4F, t, J=13.0 Hz)

XDC-3: MS m/z: 91 (PhCH$_2$); 133 (CF$_3$CF$_2$CH$_2$); 161 (CF$_3$CF$_2$CH$_2$OC); 206 (CF$_3$CF$_2$CH$_2$OC(=O)NHCH$_2$Ph); 295 (CF$_3$CF$_2$CH$_2$C(=O)NHCH$_2$PhCH); 311 (CF$_3$CF$_2$CH$_2$OC(=O)NHCH$_2$PhCH$_2$NH); 355 (CF$_3$CF$_2$CH$_2$C(=O)NHCH$_2$PhCH$_2$NHC(=O)O); 488 (CF$_3$CF$_2$CH$_2$C(=O)NHCH$_2$PhCH$_2$NHC(=O)OCH$_2$CF$_2$CF$_3$)

[Chem.26]

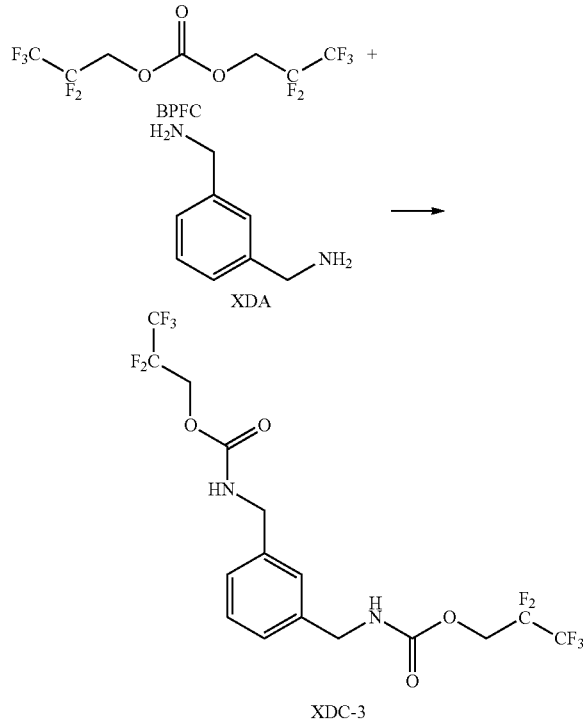

XDC-3

Example 6

Synthesis of m-xylylene dicarbamate (XDC-4)

The reaction was carried out in the same manner as Example 3 except for using 80.5 g (0.1642 mol) of bis(2,2,3,3,4,4,5,5-octafluoropentyl) carbonate (to be referred to as "BOFC" hereinafter) synthesized in the above Synthesis Example 4 in place of BTFC, and it was confirmed that m-xylylene bis(2,2,3,3,4,4,5,5-octafluoropentyl carbamate) (to be referred to as XDC-4 hereinafter) was generated as the main product (XDA base yield 98.5%). Structural assignment of the product XDC-4 was carried out by $^{19}$F-NMR and GC-Mass analyses as well as $^1$H-NMR. Analytical Results of mass fragments of XDC-4, $^1$H-NMR and $^{19}$F-NMR were shown in the following.

XDC-4: $^1$H-NMR δ: 4.279-4.300 (4H, d, J=6.31 Hz); 4.616-4.711 (4H, t, J=14.12 Hz); 6.228-6.605 (2H, tt, J=5.71 Hz); 7.174-7.338 (4H, m)

XDC-4: $^{19}$F-NMR δ: −119.413-119.583 (4F, m); −124.694 (4F, s); −129.473-129.496 (4F, m); −137.644-137.868 (4F, m)

XDC-4: MS m/z: 105 (NHCH$_2$Ph); 133 (C(=O)NHCH$_2$Ph); 147 (C(=O)NHCH$_2$PhCH$_2$); 213 (CF$_2$HCF$_2$CF$_2$CF$_2$C); 288 (CH$_2$NHC(=O)OCH$_2$CF$_2$CF$_2$CF$_2$CF$_2$H); 378 (CF$_2$HCF$_2$CF$_2$CF$_2$CH$_2$C(=O)NHCH$_2$PhCH$_2$); 449 (CF$_2$HCF$_2$CF$_2$CF$_2$CH$_2$C(=O)NHCH$_2$PhCH$_2$NHC(=O)OC)

[Chem. 27]

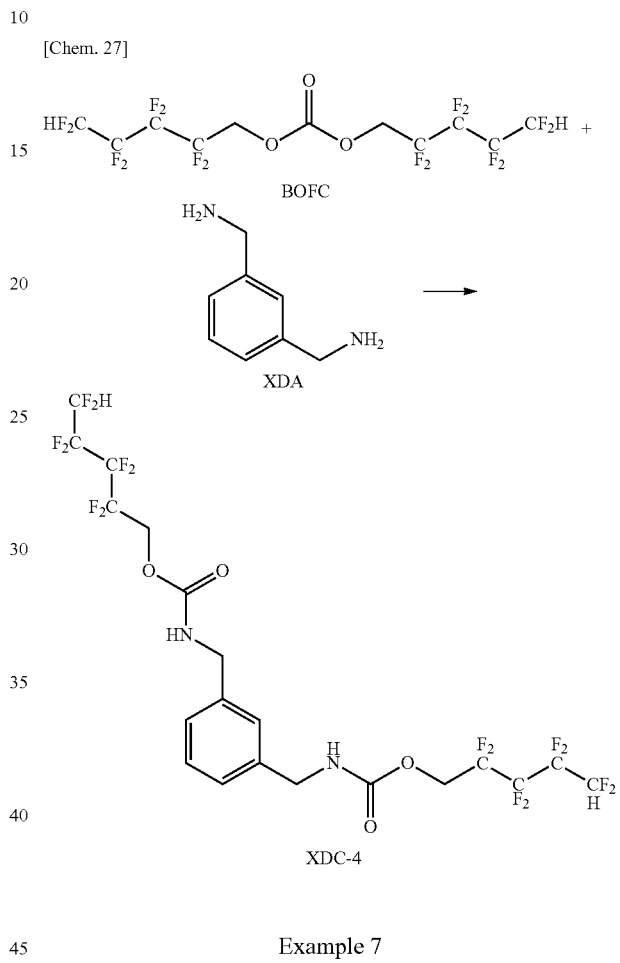

XDC-4

Example 7

Synthesis of tetrahydro-m-xylylene dicarbamate (H-XDC-1)

A 50 mL capacity glass reactor equipped with a stirrer, a 20° C. reflux condenser and a distillation line was charged with 9.20 g (0.0648 mol) of tetrahydro-m-xylenediamine (chemical agent of Tokyo Chemical Industry Co., Ltd.: Product Number of B 1005, and to be referred to as "H-XDA" hereinafter) and then heated to 50° C. while stirring. Next, 47.63 g (0.1642 mol) of bis(2,2,3,3-tetrafluoropropyl) carbonate (to be referred to as "BTFC" hereinafter) synthesized in the above Synthesis Example 1 was added dropwise thereto while adjusting the rate in such a manner that increase of the inner temperature (ΔT) becomes 10° C. or lower. After completion of the dropwise addition, the reaction was carried out while stirring at 50° C. for 1 hour. After completion of the reaction, the crude liquid was cooled to room temperature, and then a portion of the crude liquid was collected and its composition was analyzed by a $^1$H-NMR. As a result, it was confirmed that unreacted H-XDA was completely disappeared (H-XDA conversion ratio 100%) and that tetrahydrom-xylylene bis(2,2,3,3-tetrafluoropropyl carbamate) (to be referred to as H-XDC-1 hereinafter) was generated as the main product (H-XDA base yield 95.9%). H-XDC-1 as the product was obtained in a yield of 95.9%. Structural assignment of the product H-XDC-1 was carried out by $^{19}$F-NMR and GC-Mass analyses as well as $^1$H-NMR. Analytical Results of mass fragments of H-XDC-1, $^1$H-NMR and $^{19}$F-NMR were shown in the following.

H-XDC-1: $^1$H-NMR δ: 0.536-1.804 (10H, m); 2.933-2.976 (4H, t, J=6.3 Hz); 4.413-4.504 (4H, t, J=13.8 Hz); 5.927-6.276 (2H, tt, J=4.8 Hz)

H-XDC-1: $^{19}$F-NMR δ: −125.017−−125.129 (4F, m); −138.503−−138.706 (4F, d, J=56.1 Hz)

H-XDC-1: MS m/z: 51 (CF$_2$H); 95 ((C$_6$H$_9$)CH$_2$); 139 (NHCH$_2$(C$_6$H$_9$)CH$_2$NH); 167 (NHCH$_2$(C$_6$H$_9$)CH$_2$NHC(=O)); 188 (CH$_2$NHC(=O)OCH$_2$CF$_2$CF$_2$H); 240 (CH$_2$C(=O)NHCH$_2$(C$_6$H$_8$)CH$_2$NHC(=O)O); 255 (CH$_2$C(=O)NHCH$_2$(C$_6$H$_9$)CH$_2$NHC(=O)OCH$_2$); 327 (CF$_2$HCF$_2$CH$_2$C(=OD)NHCH$_2$(C$_6$H$_{10}$)CH$_2$NHC(=O)); 458 ((CF$_2$HCF$_2$CH$_2$C(=O)NHCH$_2$)$_2$(C$_6$H$_{10}$))

[Chem. 28]

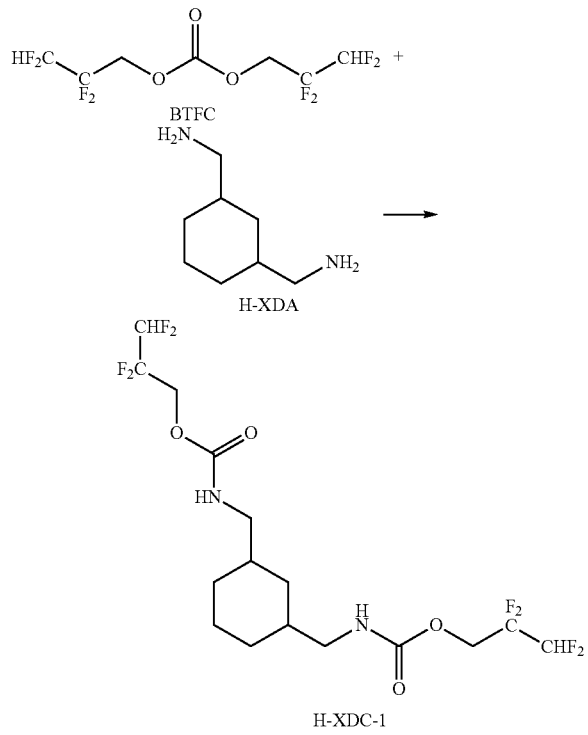

H-XDC-1

Example 8

Synthesis of tetrahydro-m-xylylene dicarbamate (H-XDC-2)

The reaction was carried out in the same manner as Example 7 except for using 37.1 g (0.1642 mol) of bis(2,2,2-trifluoroethyl) carbonate (to be referred to as "BTrFC" hereinafter) synthesized in the above Synthesis Example 2 in place of BTFC, and it was confirmed that tetrahydro-m-xylylene bis(2,2,2-trifluoroethyl carbamate) (to be referred to as H-XDC-2 hereinafter) was generated as the main product (H-XDA base yield 93.2%). Structural assignment of the product H-XDC-2 was carried out by $^{19}$F-NMR and GC-Mass analyses as well as $^1$H-NMR. Analytical Results of mass fragments of H-XDC-2, $^1$H-NMR and $^{19}$F-NMR were shown in the following.

H-XDC-2: $^1$H-NMR δ: 0.553-1.821 (10H, m); 2.991-3.033 (4H, t, J=6.31 Hz); 4.515-4.605 (4H, q, J=9.01 Hz)

H-XDC-2: $^{19}$F-NMR δ: −74.747-74.808 (6F, t, J=8.4795 Hz)

H-XDC-2: MS m/z: 83 (CF$_3$CH$_2$); 127 (CF$_3$CH$_2$C(=O)); 156 (CF$_3$CH$_2$C(=O)NHCH$_2$); 238 (CF$_3$CH$_2$C(=OC)NHCH$_2$(C$_6$H$_{10}$)); 252 (CF$_3$CH$_2$C(=O)NHCH$_2$(C$_6$H$_{10}$)CH$_2$); 295 (CF$_3$CH$_2$C(=O)NHCH$_2$(C$_6$H$_{10}$)CH$_2$NHC(=O)); 337 (CF$_3$CH$_2$C(=O)NHCH$_2$(C$_6$H$_{10}$)CH$_2$NHC(=O)OCH$_2$C); 394 (CF$_3$CH$_2$OC(=O)NHCH$_2$(C$_6$H$_{10}$)CH$_2$NHC(=O)OCH$_2$CF$_3$)

[Chem. 29]

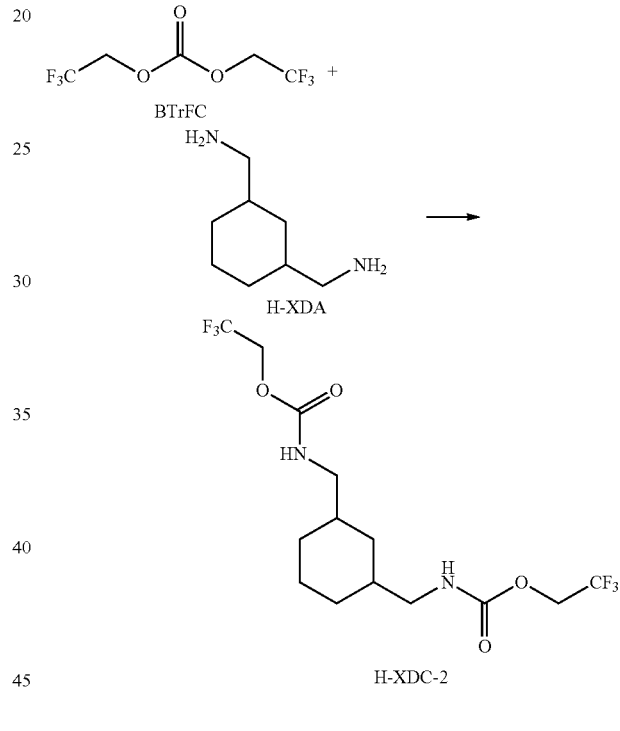

H-XDC-2

Example 9

Synthesis of tetrahydro-m-xylylene dicarbamate (H-XDC-3)

The reaction was carried out in the same manner as Example 7 except for using 53.5 g (0.1642 mol) of bis(2,2,3,3,3-pentafluoropropyl) carbonate (to be referred to as "BPFC" hereinafter) synthesized in the above Synthesis Example 3 in place of BTFC, and it was confirmed that tetrahydro-m-xylylene bis(2,2,3,3,3-pentafluoropropyl carbamate) (to be referred to as H-XDC-3 hereinafter) was generated as the main product (H-XDA base yield 95.5%). Structural assignment of the product H-XDC-3 was carried out by $^{19}$F-NMR and GC-Mass analyses as well as $^1$H-NMR. Analytical Results of mass fragments of H-XDC-3, $^1$H-NMR and $^{19}$F-NMR were shown in the following.

H-XDC-3: $^1$H-NMR δ: 0.545-1.801 (10H, m); 2.991-3.033 (4H, t, J=6.31 Hz); 4.614-4.707 (4H, t, J=12.62 Hz)

H-XDC-3: $^{19}$F-NMR δ: −84.621 (6F, s); −124.351-124.451 (4F, t, J=13.00 Hz) H-XDC-3: MS m/z: 133 (CF$_3$CF$_2$CH$_2$); 177 (CF$_3$CF$_2$CH$_2$C(=O)); 206 (CF$_3$CF$_2$CH$_2$OC(=O)NHCH$_2$); 288 (CF$_3$CF$_2$CH$_2$C(=O)NHCH$_2$(C$_6$H$_{10}$)); 317 (CF$_3$CF$_2$CH$_2$OC(=O)NHCH$_2$(C$_6$H$_{10}$)CH$_2$NH); 345 (CF$_3$CF$_2$CH$_2$OC(=O)NHCH$_2$(C$_6$H$_{10}$)CH$_2$NHC(=O); 494 (CF$_3$CF$_2$CH$_2$OC(=O)NHCH$_2$(C$_6$H$_{10}$)CH$_2$NHC(=O)OCH$_2$CF$_2$CF$_3$)

[Chem. 30]

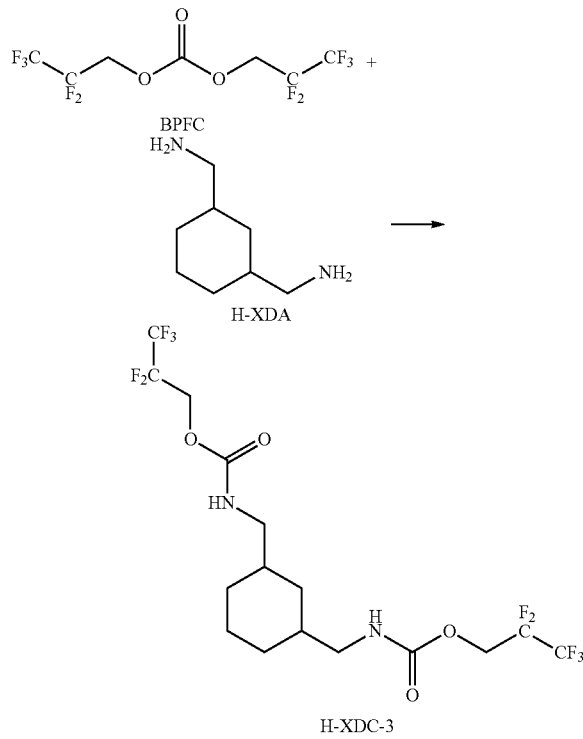

Example 10

Synthesis of tetrahydro-m-xylylene dicarbamate (H-XDC-4)

The reaction was carried out in the same manner as Example 7 except for using 80.5 g (0.1642 mol) of bis(2,2,3,3,4,4,5,5-octafluoropentyl) carbonate (to be referred to as "BOFC" hereinafter) synthesized in the above Synthesis Example 4 in place of BTFC, and it Was confirmed that tetrahydro-m-xylylene bis(2,2,3,3,4,4,5,5-octafluoropentyl carbamate) (to be referred to as H-XDC-4 hereinafter) was generated as the main product (H-XDA base yield 98.0%). Structural assignment of the product H-XDC-4 was carried out by $^{19}$F-NMR and GC-Mass analyses as well as $^1$H-NMR. Analytical Results of mass fragments of H-XDC-4, $^1$H-NMR and $^{19}$F-NMR were shown in the following.

H-XDC-4: $^1$H-NMR δ: 0.593-1.845 (10H, m); 2.971-3.038 (4H, t, J=6.6 Hz); 4.631-4.728 (4H, t, J=14.72 Hz); 6.536-6.913 (2H, tt, J=5.71 Hz)

H-XDC-4: $^{19}$F-NMR δ: −120.428-120.613 (4F, m); −125.623-125.839 (4F, m); −130.618-130.657 (4F, m); −138.774-139.028 (4F, m)

Apparatus: JMS-T100GC (manufactured by JEOL Ltd.)
Ionization method: FD method
Cathode voltage: −10 kV
Emitter current: 0 mA→51.2 mA/min→40 mA
Detector voltage: 2,500 V
Measuring mass range: m/z 3-2000

H-XDC-4: MS m/z:
658 (CHF$_2$(CF$_2$)$_3$CH$_2$O(O=)CNHCH$_2$(C$_6$H$_{10}$)CH$_2$NHC(=O)OCH$_2$(CF$_2$)$_3$CHF)

[Chem. 31]

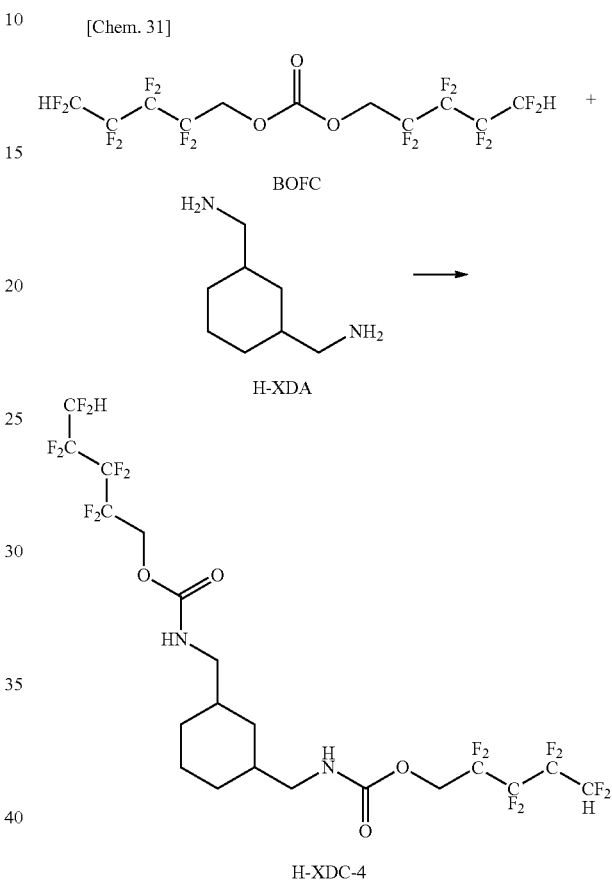

Example 11

Synthesis of dicyclohexylmethane-4,4'-dicarbamate (H-MDC-1)

A 50 mL capacity glass reactor equipped with a stirrer, a 20° C. reflux condenser and a distillation line was charged with 13.6 g (0.0648 mol) of 4,4'-diamino(dicyclohexylmethane) (chemical agent of Tokyo Chemical Industry Co., Ltd.: Product Number of M0699, and to be referred to as "H-MDA" hereinafter) and then heated to 50° C. while stirring. Next, 47.63 g (0.1642 mol) of bis(2,2,3,3-tetrafluoropropyl) carbonate (to be referred to as "BTFC" hereinafter) synthesized in the above Synthesis Example 1 was added dropwise thereto while adjusting the rate in such a manner that increase of the inner temperature (ΔT) becomes 10° C. or lower. After completion of the dropwise addition, the reaction was carried out while stirring at 50° C. for 1 hour. After completion of the reaction, the crude liquid was cooled to room temperature, and then a portion of the crude liquid was collected and its composition was analyzed by a $^1$H-NMR. As a result, it was confirmed that unreacted H-MDA was completely disappeared (H-MDA conversion ratio 100%) and that dicyclohexylmethane-4,4'-bis(2,2,3,3-tetrafluoropropyl carbamate) (to be referred to as H-MDC-1 hereinafter) was generated as the main product (H-MDA base yield 92.9%). H-MDC-1 as the product was obtained in a yield of 92.9%. Structural assignment of the product H-MDC-1 was carried out by $^{19}$F-NMR and GC-Mass analyses as well as $^{1}$H-NMR. Analytical Results of mass fragments of H-MDC-1, $^{1}$H-NMR and $^{19}$F-NMR were shown in the following.

H-MDC-1: $^{1}$H-NMR δ: 0.889-1.942 (20H, m); 3.279-3.409 (2H, m); 4.431-4.523 (4H, t, J=13.82 Hz); 6.082-6.465 (2H, tt, J=5.11 Hz)

H-MDC-1: $^{19}$F-NMR δ: −126.263-126.394 (4F, m); −439.745-139.930 (4F, d, J=52.29 Hz)

H-MDC-1: MS m/z: 81 (($C_6H_9$)); 95 (($C_6H_9$)$CH_2$; 110 (HN($C_6H_9$)$CH_2$); 138 ((O=)CHN($C_6H_9$)$CH_2$); 179 (($C_6H_{11}$)$CH_2$($C_6H_{10}$)); 190 (N($C_6H_9$)$CH_2$($C_6H_9$)); 205 (N($C_6H_9$)$CH_2$($C_6H_{10}$)N); 217 (N($C_6H_9$)$CH_2$($C_6H_{10}$)NC); 232 (CNH($C_6H_{11}$)$CH_2$($C_6H_{10}$)NHC); 262 (C(=O)N($C_6H_{10}$)$CH_2$($C_6H_{10}$)NC(=O)); 310 (O(O=C)NH($C_6H_{10}$)$CH_2$($C_6H_{10}$)NHC(=O)OCH$_2$)

[Chem. 32]

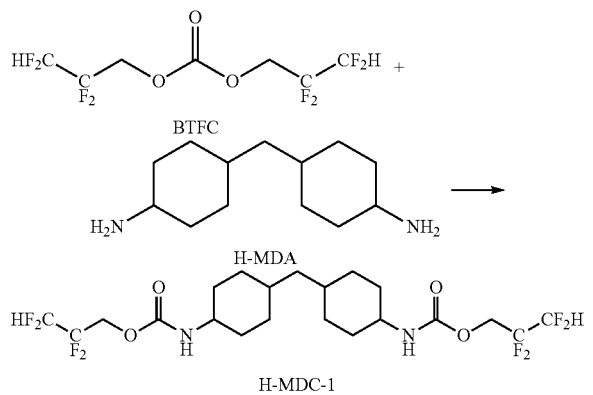

Example 12

Synthesis of dicyclohexylmethane-4,4'-dicarbamate (H-MDC-2)

The reaction was carried out in the same manner as Example 11 except for using 37.1 g (0.1642 mol) of bis(2,2,2-trifluoroethyl) carbonate (to be referred to as "BTrFC" hereinafter) synthesized in the above Synthesis Example 2 in place of BTFC, and it was confirmed that dicyclohexylmethane-4,4'-bis(2,2,2-trifluoroethyl carbamate) (to be referred to as H-MDC-2 hereinafter) was generated as the main product (H-MDA base yield 90.2%). Structural assignment of the product H-MDC-2 was carried out by $^{19}$F-NMR and GC-Mass analyses as well as $^{1}$H-NMR. Analytical Results of mass fragments of H-MDC-2, $^{1}$H-NMR and $^{19}$F-NMR were shown in the following.

H-MDC-2: $^{1}$H-NMR δ: 0.676-1.728 (20H, m); 3.066-3.197 (2H, m); 4.227-4.367 (4H, q, J=9.012 Hz)

H-MDC-2: $^{19}$F-NMR δ: −74.927-75.043 (6F, t, J=8.76 Hz)

H-MDC-2: MS m/z: 81 (CF$_3$C); 95 (($C_6H_9$)$CH_2$); 127 (CF$_3$CH$_2$C(=O)); 206 (N($C_6H_{10}$)$CH_2$($C_6H_{10}$)N); 219 (N($C_6H_{10}$)$CH_2$($C_6H_{10}$)NHC); 262 (C(=O)N($C_6H_{10}$)$CH_2$($C_6H_{10}$)NHC(=O)); 344 (N($C_6H_{10}$)$CH_2$($C_6H_{10}$)NHC(=O)OCH$_2$CF$_3$); 362 (C(=O)N($C_6H_{10}$)$CH_2$($C_6H_{10}$)NHC(=O)OCH$_2$CF$_3$)

[Chem. 33]

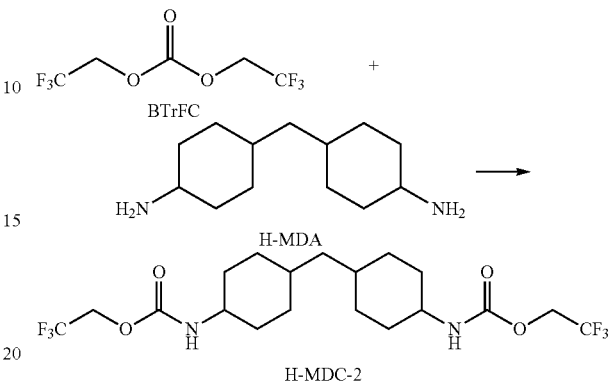

Example 13

Synthesis of dicyclohexylmethane-4,4'-dicarbamate (H-MDC-3)

The reaction was carried out in the same manner as Example 11 except for using 53.5 g (0.1642 mol) of bis(2,2,3,3,3-pentafluoropropyl) carbonate (to be referred to as "BPFC" hereinafter) synthesized in the above Synthesis Example 3 in place of BTFC, and it was confirmed that dicyclohexylmethane-4,4'-bis(2,2,3,3,3-pentafluoropropyl carbamate) (to be referred to as H-MDC-3 hereinafter) was generated as the main product (H-MDA base yield 91.5%). Structural assignment of the product H-MDC-3 was carried out by $^{19}$F-NMR and GC-Mass analyses as well as $^{1}$H-NMR. Analytical Results of mass fragments of H-XDC-3, $^{1}$H-NMR and $^{19}$F-NMR were shown in the following.

H-MDC-3: $^{1}$H-NMR δ: 0.915-1.942 (20H, m); 3.302-3.406 (2H, m); 4.598-4.689 (4H, t, J=13.82 Hz)

H-MDC-3: $^{19}$F-NMR δ: −84.432 (4H, s); −124.089-124.184 (6F, t, J=13.00 Hz)

H-MDC-3: MS m/z: 81 (CF$_3$C), ($C_6H_9$); 95 (($C_6H_9$)$CH_2$); 133 (CF$_3$CF$_2$CH$_2$); 177 (CF$_3$CF$_2$CH$_2$C(=O)); 191 (CF$_3$CF$_2$CH$_2$C(=O)N); 206 (N($C_6H_{10}$)$CH_2$($C_6H_{10}$)N); 219 (N($C_6H_{10}$)$CH_2$($C_6H_{10}$)NHC); 232 (CNH($C_6H_{10}$)$CH_2$($C_6H_{10}$)NHC); 263 (C(=O)NH($C_6H_{10}$)$CH_2$($C_6H_{10}$)NHC(=O)); 384 (N($C_6H_{10}$)$CH_2$($C_6H_{10}$)NHC(=O)OCH$_2$CF$_2$CF$_3$); 412 (C(=O)N($C_6H_{10}$)$CH_2$($C_6H_{10}$)NHC(=O)OCH$_2$CF$_2$CF$_3$)

[Chem. 34]

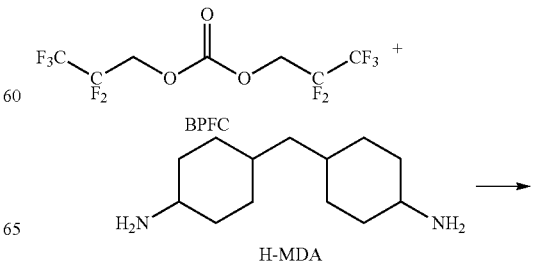

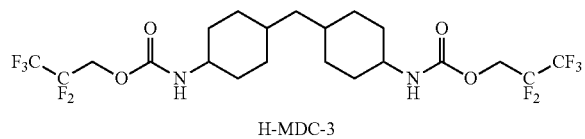

H-MDC-3

Example 14

Synthesis of dicyclohexylmethane-4,4'-dicarbamate (H-MDC-4)

The reaction was carried out in the same manner as Example 11 except for using 80.5 g (0.1642 mol) of bis(2,2,3,3,4,4,5,5-octafluoropentyl) carbonate (to be referred to as "BOFC" hereinafter) synthesized in the above Synthesis Example 4 in place of BTFC, and it was confirmed that dicyclohexylmethane-4,4'-bis(2,2,3,3,4,4,5,5-octafluoropentyl carbamate) (to be referred to as H-MDC-4 hereinafter) was generated as the main product (H-MDA base yield 93.0%). Structural assignment of the product H-MDC-4 was carried out by $^{19}$F-NMR and GC-Mass analyses as well as $^{1}$H-NMR. Analytical Results of mass fragments of H-MDC-4, $^{1}$H-NMR and $^{19}$F-NMR were shown in the following.

H-MDC-4: $^{1}$H-NMR δ: 0.907-2.028 (20H, m); 3.416-3.442 (2H, m); 4.518-4.611 (4H, t, J=14.12 Hz); 5.850-6.232 (2H, tt, J=5.41 Hz)

H-MDC-4: $^{19}$F-NMR δ: −120.593-120.697 (4F, m); −125.965 (4F, s); −130.575 (4F, s); −137.598-137.783 (4F, d, J=52.29 Hz)

Apparatus: JMS-T100GC (manufactured by JEOL Ltd.)
Ionization method: FD method
Cathode voltage: −10 kV
Emitter current: 0 mA→51.2 mA/min→40 mA
Detector voltage: 2,500 V
Measuring mass range: m/z 3-2000

H-MDC-4: MS m/z:
726 (CHF$_2$(CF$_2$)$_3$CH$_2$O(O=)CNH(C$_6$H$_{10}$)CH$_2$(C$_6$H$_{10}$)NHC(=O)OCH$_2$(CF$_2$)$_3$CHF)

Example 15

Synthesis of isophorone dicarbamate (IPDC-1)

A 500 mL capacity glass reactor equipped with a stirrer, a 20° C. reflux condenser and a dripping funnel was charged with 344.90 g (1.19 mol) of bis(2,2,3,3-tetrafluoropropyl) carbonate (to be referred to as "BTFC" hereinafter) synthesized in the above Synthesis Example 1 and then heated to 60° C. while stirring. Next, 49.66 g (0.292 mol) of isophoronediamine (chemical agent of Tokyo Chemical Industry Co., Ltd.: Product Number of 10228, and to be referred to as "IPDA" hereinafter) was added dropwise thereto while adjusting the rate with careful attention to increase of the inner temperature (ΔT). After completion of the dropwise addition, the reaction system was stirred at 100° C. for 1 hour, and then heated to 120° C. with careful attention to exothermic degree, so that the heating was carried out for 5 hours in total. After completion of the reaction, the crude liquid was cooled to room temperature, and then a portion of the crude liquid was collected and subjected to IR spectral measurement. The completion of the reaction was confirmed from the disappearance of N—H absorption derived formamine (2900 cm$^{-1}$ to 2950 cm$^{-1}$) and the appearance of carbonyl absorption derived from carbamate (1710 cm$^{-1}$ to 1740 cm$^{-1}$). The crude liquid was distilled under reduced pressure, and thereby recovering 76.21 g (0.577 mol) of 2,2,3,3-tetrafluoro-1-propanol by-produced in the reaction and unreacted 173 g (0.597 mol) of BTFC. Finally, 140.2 g (0.288 mol) of isophorone bis(2,2,3,3-tetrafluoro-n-propyl) carbamate (to be referred to as IPDC-1 hereinafter) was recovered. IPDC-1 as the target product was obtained in a yield of 98.8% (IPDA base). Structural assignment of the IPDC-1 was carried out by IR and chemical ionization mass spectrometry (CI-Mass) using methane gas. Analytical Results of CI-Mass fragments of IPDC-1 were shown in Table 2.

[Chem. 35]

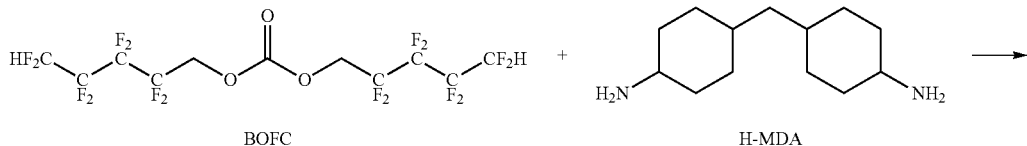

BOFC + H-MDA →

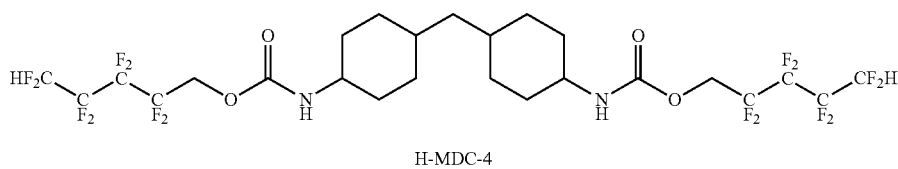

H-MDC-4

TABLE 2

| Structural Formula | m/z |
|---|---|
| HF$_2$C-CF$_2$-O-C(=O)-NH-[isophorone]-CH$_2$-NH-C(=O)-O-CF$_2$-CF$_2$H | 467[M − 19], 487[M + 1]<br>515[M + 29], 527[M + 41] |

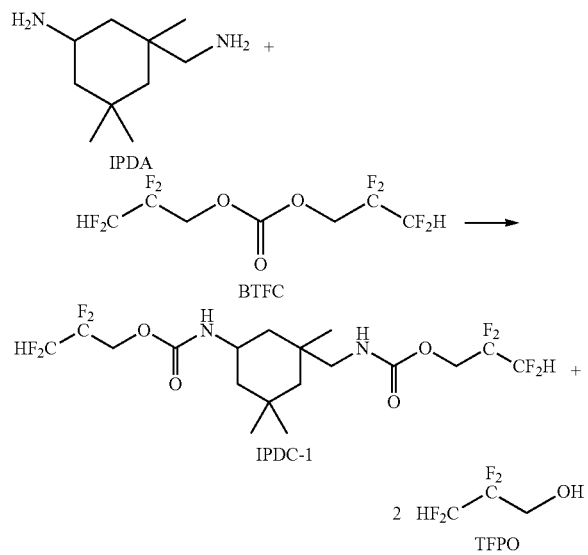

Example 16

Synthesis of isophorone dicarbamate (IPDC-2)

The reaction was carried out in the same manner as Example 15 except for using 269 g (1.19 mol) of bis(2,2,2-trifluoroethyl) carbonate (to be referred to as "BTrFC" hereinafter) synthesized in the above Synthesis Example 2 in place of BTFC, and 120.3 g (0.285 mol) of isophorone bis(2,2,2-trifluoroethyl) carbamate (to be referred to as IPDC-2 hereinafter) was recovered. IPDC-2 as the target product was obtained in a yield of 97.6% (IPDA base). Structural assignment of the IPDC-2 was carried out by IR (carbonyl absorption derived from carbamate (1710 cm$^{-1}$ to 1740 cm$^{-1}$)) and chemical ionization mass spectrometry (CI-Mass) using methane gas. Analytical Results of CI-Mass fragments of IPDC-2 were shown in Table 3.

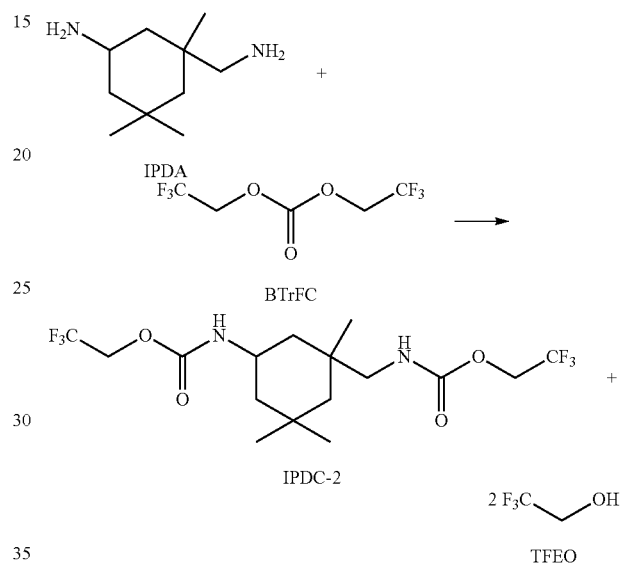

Example 17

Synthesis of isophorone dicarbamate (IPDC-3)

The reaction was carried out in the same manner as Example 15 except for using 388 g (1.19 mol) of bis(2,2,3,3,3-pentafluoropropyl) carbonate (to be referred to as "BPFC" hereinafter) synthesized in the above Synthesis Example 3 in place of BTFC, and 150.8 g (0.289 mol) of isophorone bis(2,2,3,3,3-pentafluoropropyl) carbamate (to be referred to as IPDC-3 hereinafter) was recovered. IPDC-3 as the target product was obtained in a yield of 99.0% (IPDA base). Structural assignment of the IPDC-3 was carried out by IR (carbonyl absorption derived from carbamate (1710 cm$^{-1}$ to 1740 cm$^{-1}$)) and chemical ionization mass spectrometry (CI-Mass) using methane gas. Analytical Results of CI-Mass fragments of IPDC-3 were shown in Table 4.

TABLE 3

| Structural Formula | m/z |
|---|---|
| F$_3$C-CH$_2$-O-C(=O)-NH-[isophorone]-CH$_2$-NH-C(=O)-O-CH$_2$-CF$_3$ | 403[M − 19], 423[M + 1]<br>451[M + 29], 463[M + 41] |

TABLE 4

| Structural Formula | m/z |
|---|---|
| 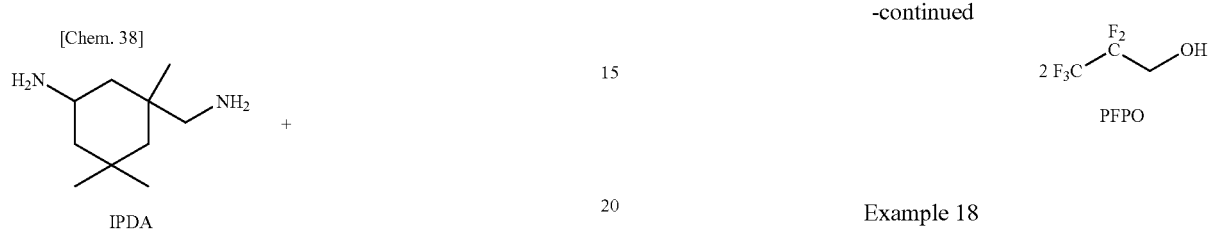 | 503[M − 19], 523[M + 1]<br>551[M + 29], 563[M + 41] |

[Chem. 38]

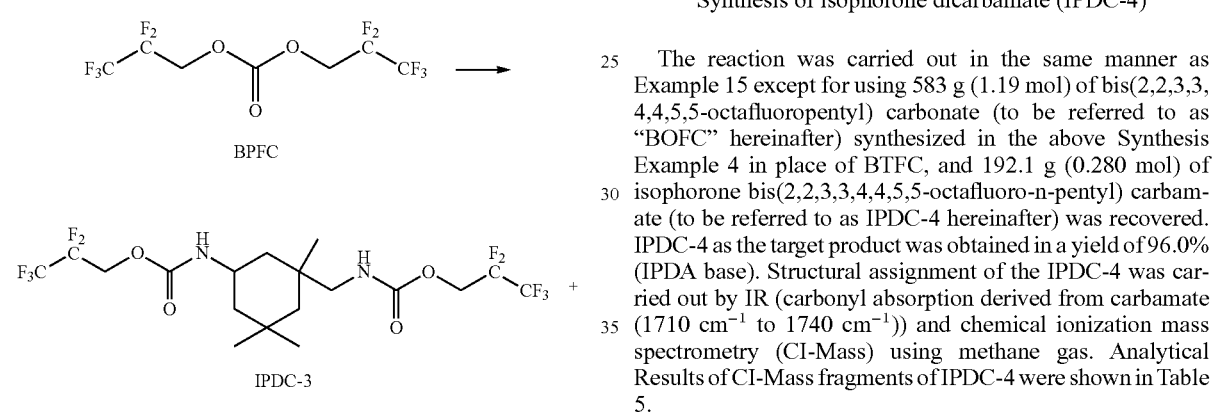

Example 18

Synthesis of isophorone dicarbamate (IPDC-4)

The reaction was carried out in the same manner as Example 15 except for using 583 g (1.19 mol) of bis(2,2,3,3,4,4,5,5-octafluoropentyl) carbonate (to be referred to as "BOFC" hereinafter) synthesized in the above Synthesis Example 4 in place of BTFC, and 192.1 g (0.280 mol) of isophorone bis(2,2,3,3,4,4,5,5-octafluoro-n-pentyl) carbamate (to be referred to as IPDC-4 hereinafter) was recovered. IPDC-4 as the target product was obtained in a yield of 96.0% (IPDA base). Structural assignment of the IPDC-4 was carried out by IR (carbonyl absorption derived from carbamate (1710 $cm^{-1}$ to 1740 $cm^{-1}$)) and chemical ionization mass spectrometry (CI-Mass) using methane gas. Analytical Results of CI-Mass fragments of IPDC-4 were shown in Table 5.

TABLE 5

| Structural Formula | m/z |
|---|---|
| 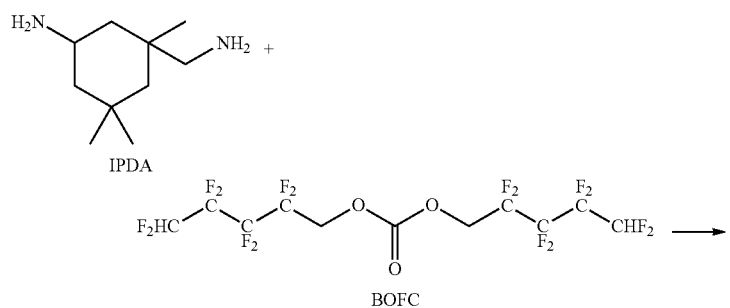 | 667[M − 19], 687[M + 1]<br>715[M + 29], 727[M + 41] |

[Chem. 39]

-continued

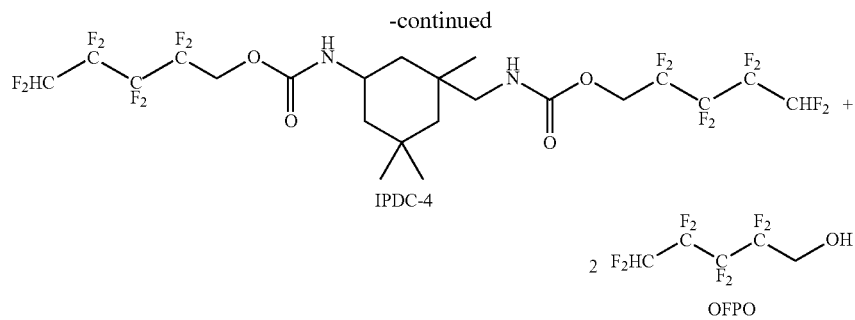

IPDC-4

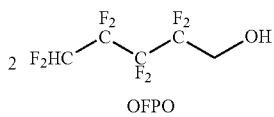

OFPO

Example 19

Synthesis of isophorone diisocyanate (IPDI)

A 1 mg of isophorone bis(2,2,3,3-tetrafluoro-n-propyl) carbamate (IPDC-1) was introduced into a pyrolyzer of a gas chromatograph which has an inlet equipped with the pyrolyzer, thermal decomposed under helium gas atmosphere at 290° C. for 1 second, and then total amount of the product were introduced into the gas chromatograph apparatus together with the helium carrier gas. The generation of IPDI was confirmed by carrying out a gas chromatography analysis and comparing with an available standard article. Yield of the IPDI based on IPDC-1 calculated from peak area of gas chromatograph was 50% by mol.

While the invention has been described in detail and with reference to specific embodiments thereof, it will be apparent to one skilled in the art that various changes and modifications can be made therein without departing from the spirit and scope thereof.

The present application is based on Japanese Patent Application No. 2010-086126 filed on Apr. 2, 2010, and the contents are incorporated herein by reference.

INDUSTRIAL APPLICABILITY

The isocyanate compounds obtained by the production method of the present invention are useful for materials, for example, various urethane compounds, urea compounds, and polyurethanes.

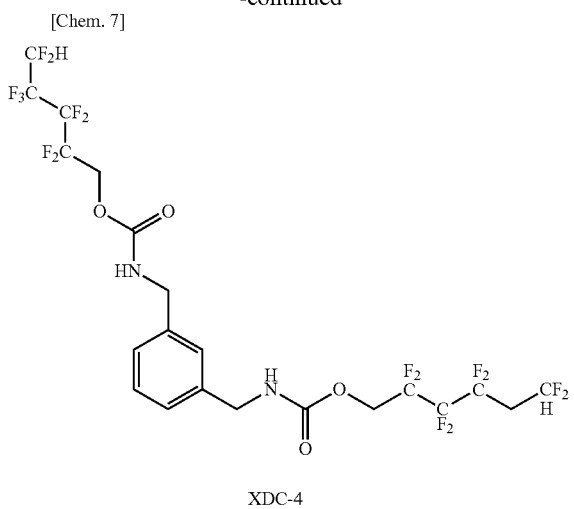

The invention claimed is:

1. A carbamate compound selected from the group consisting of the carbamate compounds represented by formulae (4) to (11):

[Chem. 4]

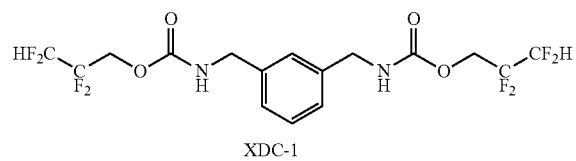

XDC-1

[Chem. 5]

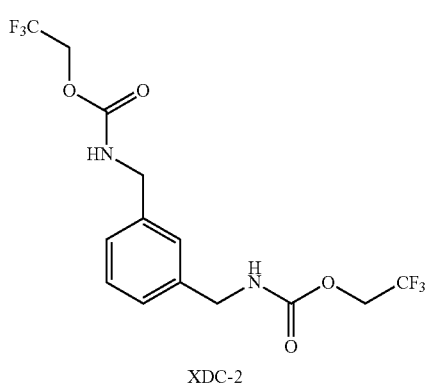

XDC-2

[Chem. 6]

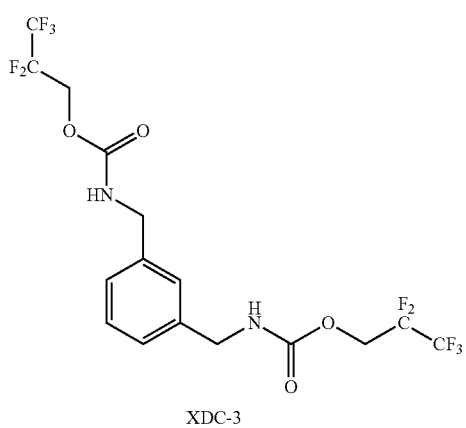

XDC-3